US012629007B2

(12) United States Patent 
Suzuki et al.

(10) Patent No.: US 12,629,007 B2 
(45) Date of Patent: May 19, 2026

(54) INSERTION-INSTRUMENT BENDING OPERATION MECHANISM AND INSERTION INSTRUMENT

(71) Applicant: OLYMPUS CORPORATION, Tokyo (JP)

(72) Inventors: Motohiko Suzuki, Sagamihara (JP); Takuto Yoshinaga, Hino (JP); Tsukasa Ota, Hachioji (JP); Wataru Matsuura, Fuchu (JP); Keita Mitsuhashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 678 days.

(21) Appl. No.: 17/835,190

(22) Filed: Jun. 8, 2022

(65) Prior Publication Data

US 2022/0296078 A1 Sep. 22, 2022

Related U.S. Application Data

(63) Continuation of application No. PCT/JP2019/048813, filed on Dec. 12, 2019.

(51) Int. Cl.
*A61B 1/005* (2006.01)
*A61B 1/00* (2006.01)
(52) U.S. Cl.
CPC ............ *A61B 1/0052* (2013.01); *A61B 1/005* (2013.01); *A61B 1/0057* (2013.01); *A61B 1/00042* (2022.02)
(58) Field of Classification Search
CPC .............. A61B 1/00066; A61B 1/0052; A61B 1/0057; A61B 1/008; A61B 1/005;
(Continued)

(56) References Cited

U.S. PATENT DOCUMENTS 8,608,649 B2 12/2013 McWeeney et al.
2008/0319265 A1* 12/2008 Masaki ................ A61B 1/0052
600/146
(Continued)

FOREIGN PATENT DOCUMENTS

CN 103619230 A 3/2014
JP H10-286220 A 10/1998
(Continued)

OTHER PUBLICATIONS

International Search Report dated Mar. 3, 2020 received in PCT/JP2019/048813.

*Primary Examiner* — Ryan N Henderson
*Assistant Examiner* — Pamela F Wu
(74) *Attorney, Agent, or Firm* — Scully, Scott, Murphy & Presser, P.C.

(57) ABSTRACT

A bending operation mechanism includes a bending operation member configured to bend a bending portion, a wire pulling member configured to rotate along with rotation of the bending operation member, a lock operation member supported to a rotational axis, a cam member having a cam surface and integrally provided with the lock operation member, and a brake member having a cam follower surface capable of sliding relative to the cam surface. The cam member moves along with rotation of the lock operation member. The brake member moves in a direction in which a contact surface contacts a circumference of the wire pulling member as the cam follower surface slides on the cam surface in accordance with movement of the cam member.

20 Claims, 17 Drawing Sheets

(58) Field of Classification Search
CPC ................ A61B 1/0051; A61M 25/01; A61M
25/0105; A61M 25/0133; A61M 25/0136;
A61M 25/0147
USPC .................................................. 600/146, 148
See application file for complete search history.

(56) References Cited

U.S. PATENT DOCUMENTS

| | | | |
|---|---|---|---|
| 2009/0287188 A1 * | 11/2009 | Golden ................ | A61B 1/0052 |
| | | | 604/528 |
| 2013/0190566 A1 | 7/2013 | Miyoshi et al. | |
| 2014/0058323 A1 | 2/2014 | Hoshino | |
| 2014/0088497 A1 * | 3/2014 | Campbell ............ | A61B 1/0052 |
| | | | 604/95.04 |
| 2018/0028048 A1 | 2/2018 | Simmons et al. | |

FOREIGN PATENT DOCUMENTS

| | | | |
|---|---|---|---|
| JP | H10-295628 A | 11/1998 | |
| JP | 2003-061903 A | 3/2003 | |
| JP | 2019-080683 A | 5/2019 | |
| WO | 2013061690 A1 | 5/2013 | |
| WO | 2016/027521 A1 | 2/2016 | |

* cited by examiner

INSERTION-INSTRUMENT BENDING OPERATION MECHANISM AND INSERTION INSTRUMENT

CROSS REFERENCE TO RELATED APPLICATION

This application is a continuation application of PCT/JP2019/048813 filed on Dec. 12, 2019, the entire contents of which are incorporated herein by this reference.

BACKGROUND OF THE INVENTION

1. Field of the Invention

The present invention relates to an insertion-instrument bending operation mechanism and particularly relates to an insertion-instrument bending operation mechanism and an insertion instrument that include a mechanism for an operation to bend a bending portion of an insertion portion of an endoscope.

2. Description of the Related Art

An endoscope system including an endoscope and a video processor or the like is widely used in, for example, medical and industrial fields, the endoscope being configured to pick up an image of an object inside a subject, the video processor or the like being configured to provide predetermined image processing to an observation image of the object picked up by the endoscope and output the observation image.

An endoscope used in such an endoscope system typically includes an elongated insertion portion that is inserted into a body cavity of a subject or the like. The insertion portion includes a rigid distal end portion provided on a distal end side, a bending portion that is freely bendable and provided at a rear end of the distal end portion, and an elongated flexible tube portion provided at a rear end of the bending portion. Typically in such an endoscope, an operation portion for operating the bending portion is continuously provided on a proximal end side of the insertion portion. In a widely known endoscope, the operation portion is provided with a bending operation handle for an operation to bend the bending portion.

In a typical operation method, the bending portion of the insertion portion of an endoscope is locked in a state that the bending portion is bent. However, when operability is taken into consideration, it is desirable that the operation to lock the bending portion can be performed by an operator while grasping the bending operation handle of the operation portion. It is also desirable that the locking can be simultaneously performed in two axial directions (a U/D direction and an R/L direction) through a one-action operation.

With consideration on such requirements, U.S. Pat. No. 8,608,649 discloses a technology of locking a pulley connected to an angle wire by pressing a predetermined brake mechanism member against the pulley in a thrust direction (axial direction).

SUMMARY OF THE INVENTION

An insertion-instrument bending operation mechanism according to an aspect of the present invention includes a bending operation member, a wire pulling member, a lock operation member, a cam member, and a brake member. The bending operation member is rotatably supported about a rotational axis and configured to bend a bending portion in a predetermined direction. The bending portion is provided at an insertion portion. The wire pulling member is supported to rotate about the rotational axis along with rotation of the bending operation member and has a circumference of a predetermined radius. The lock operation member is rotatably supported about an axis center at the rotational axis. The cam member is integrally provided with the lock operation member, disposed outside the wire pulling member in a radial direction of the rotational axis, and has a cam surface facing a center of the rotational axis. The brake member is disposed between the circumference of the wire pulling member and the cam surface of the cam member and has a first surface and a second surface. The first surface is capable of sliding relative to the cam surface. The second surface is capable of contacting the circumference of the wire pulling member.

An insertion-instrument bending operation mechanism according to another aspect of the present invention includes a bending operation handle, a pulley, a lock lever, a cam member, and a brake. The bending operation handle is rotatably supported about a rotational axis and configured to bend a bending portion in a predetermined direction. The bending portion is provided at an insertion portion. The pulley is supported to rotate about the rotational axis along with rotation of the bending operation handle and has a circumference of a predetermined radius. The lock lever is rotatably supported about an axis center at the rotational axis. The cam member is integrally provided with the lock lever, disposed outside the wire pulling member in a radial direction of the rotational axis, and has a cam surface facing a center of the rotational axis. The brake is disposed between the circumference of the wire pulling member and the cam surface of the cam member and has a first surface and a second surface. The first surface is capable of sliding relative to the cam surface. The second surface is capable of contacting the circumference of the wire pulling member.

An insertion instrument according to another aspect of the present invention includes a bending operation mechanism. The bending operation mechanism includes a bending operation member, a wire pulling member, a lock operation member, a cam member, and a brake member. The bending operation member is rotatably supported about a rotational axis and configured to bend a bending portion in a predetermined direction. The bending portion is provided at an insertion portion. The wire pulling member is supported to rotate about the rotational axis along with rotation of the bending operation member and has a circumference of a predetermined radius. The lock operation member is rotatably supported about an axis center at the rotational axis. The cam member is integrally provided with the lock operation member, disposed outside the wire pulling member in a radial direction of the rotational axis, and has a cam surface facing a center of the rotational axis. The brake member is disposed between the circumference of the wire pulling member and the cam surface of the cam member and has a first surface and a second surface. The first surface is capable of sliding relative to the cam surface. The second surface is capable of contacting the circumference of the wire pulling member.

BRIEF DESCRIPTION OF THE DRAWINGS

FIG. 8 is a diagram of inside of the operation portion of a baby endoscope according to a first modification of the first embodiment when viewed from the back surface side, illustrating the unlocked state of the bending operation mechanism;

FIG. 9 is a diagram of an inside of the operation portion of the baby endoscope according to the first modification of the first embodiment when viewed from the back surface side, illustrating the locked state of the bending operation mechanism;

DETAILED DESCRIPTION OF THE PREFERRED EMBODIMENT(S)

Figure 1:
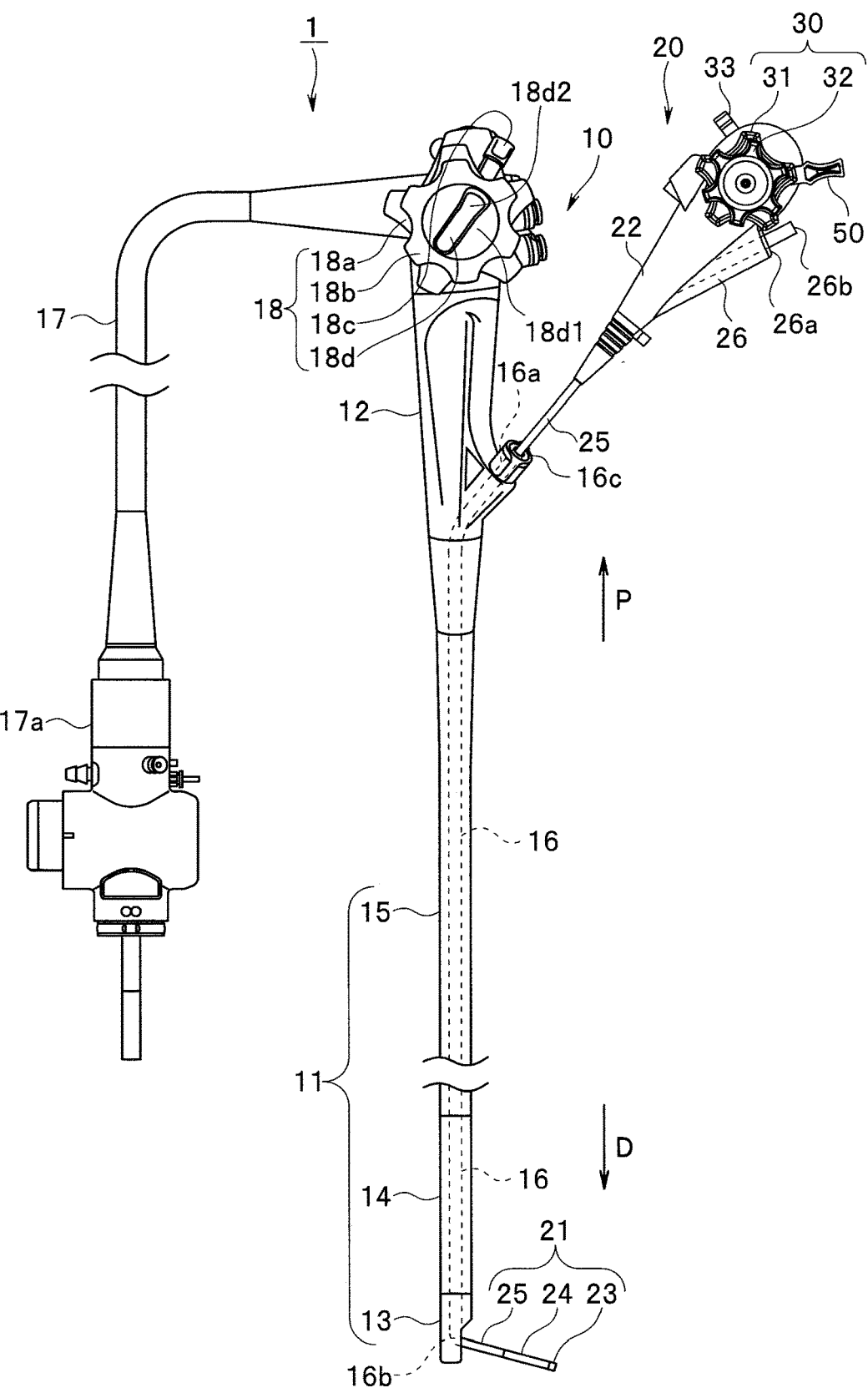
FIG. 1 is an exterior diagram illustrating an endoscope system including an endoscope (baby endoscope) and a mother endoscope to which the baby endoscope is applied, the baby endoscope incorporating an insertion-instrument bending operation mechanism according to a first embodiment of the present invention.

Embodiments of the present invention will be described below with reference to the accompanying drawings.

Note that, in a drawing used in description below, a scale is changed for each constituent component in some cases to set a size in which the constituent component is recognizable in the drawing. The present invention is not limited to the number of constituent components, shapes of the constituent components, size ratios of the constituent components, and relative positional relations among the constituent components illustrated in the drawings.

First Embodiment

The following describes an endoscope incorporating an insertion-instrument bending operation mechanism according to a first embodiment of the present invention. In the present embodiment, the endoscope is assumed to be what is called a cholangioscope used for observation and medical treatment of the inside of a bile duct (including inside of a common bile duct) or the inside of a pancreatic duct. In the following description, the endoscope (cholangioscope) according to the present embodiment is assumed to be a baby endoscope applied to a mother endoscope in what is called a mother-baby endoscope system.

FIG. 1 is an exterior diagram illustrating an endoscope system including an endoscope (baby endoscope) and a mother endoscope to which the baby endoscope is applied, the baby endoscope incorporating the insertion-instrument bending operation mechanism according to the first embodiment of the present invention. Note that, in FIG. 1 and other diagrams, an arrow P indicates a proximal end side (proximal end direction), and an arrow D indicates a distal end side (distal end direction).

A mother endoscope 10 in an endoscope system 1 according to the present embodiment illustrated in FIG. 1 is, for example, a duodenum endoscope, and a baby endoscope 20 as an endoscope of the present embodiment is a small-diameter endoscope that is inserted into a treatment instrument insertion channel 16 of the mother endoscope 10. When the baby endoscope 20 is used for observation or medical treatment inside a bile duct (common bile duct) or a pancreatic duct, the baby endoscope 20 is protruded into a body cavity from a distal end portion of the mother endoscope 10 inserted into a duodenum and only the baby endoscope 20 is selectively inserted into the bile duct or the pancreatic duct from a duodenal papilla.

First, a configuration of the mother endoscope 10 in the endoscope system 1 will be described below. As illustrated in FIG. 1, the mother endoscope 10 includes an elongated shape insertion portion 11 that is inserted into a subject, and an operation portion 12 continuously provided on the proximal end side of the insertion portion 11. The operation portion 12 is provided with various operation members that are necessary for operating the mother endoscope 10.

The insertion portion 11 includes, sequentially from the distal end side toward the proximal end side, a distal end portion body 13, a bending portion 14, and a flexible tube portion 15, which are continuously provided.

For example, an illumination optical system configured to emit illumination light transmitted from a non-illustrated light guide bundle, an objective optical system, and an image pickup device are disposed in the distal end portion body 13 of the insertion portion 11. The image pickup device of the mother endoscope 10 is configured as, for example, a CCD image sensor or a CMOS image sensor.

The bending portion 14 of the insertion portion 11 is bendable in all directions about an insertion axis, including, for example, up-down and right-left (U/D and R/L) directions.

The flexible tube portion 15 of the insertion portion 11 is configured as a flexible tubal member. For example, the treatment instrument insertion channel 16, a non-illustrated image pickup cable, the light guide bundle, and an air-water feeding tube are disposed inside the flexible tube portion 15.

The treatment instrument insertion channel 16 (in the mother endoscope 10) extends from the distal end portion body 13 of the insertion portion 11 to the operation portion 12. The treatment instrument insertion channel 16 includes a proximal end side opening 16a on the distal end side of a bending operation portion 18 of the operation portion 12, which will be described later, and includes a distal end side opening 16b at the distal end portion body 13 of the insertion portion 11.

For example, a forceps plug 16c including a check valve (backflow prevention valve) is attached to the proximal end side opening 16a of the operation portion 12.

The treatment instrument insertion channel 16 allows insertion of, through the forceps plug 16c, an insertion portion 21 of the baby endoscope 20 as an endoscope incorporating an insertion-instrument bending operation mechanism 35 (refer to FIG. 4, for example) according to the present embodiment, and also allows insertion of another treatment instrument or the like.

The bending operation portion 18 for an operation to bend the bending portion 14 is provided on the proximal end side of the proximal end side opening 16a of the operation portion 12. The bending operation portion 18 includes a UD bending operation knob 18a, an RL bending operation knob 18b, a UD braking lever 18c, and an RL braking grip 18d. The RL braking grip 18d includes a disk portion 18d1, and a rectangular portion 18d2 protruding from the disk portion 18d1.

The UD bending operation knob 18a, the RL bending operation knob 18b, the UD braking lever 18c, and the RL braking grip 18d are rotation operation members configured to be coaxially rotatable about a predetermined central axis.

The UD bending operation knob 18a is a rotation operation member for an operation to bend the bending portion 14 in the up-down direction (U/D direction). When the UD bending operation knob 18a is rotated in one direction, the bending portion 14 bends in a U direction (up direction). When the UD bending operation knob 18a is rotated in the other direction, the bending portion 14 bends in a D direction (down direction).

The RL bending operation knob 18b is a rotation operation member for an operation to bend the bending portion 14 in the right-left direction (R/L direction). When the RL bending operation knob 18b is rotated in one direction, the bending portion 14 bends in an R direction (right direction). When the RL bending operation knob 18b is rotated in the other direction, the bending portion 14 bends in an L direction (left direction).

It is possible to perform an operation to bend the bending portion 14 in all directions about the insertion axis as described above by combining bending (in the U/D direction) through the UD bending operation knob 18a and bending (in the R/L direction) through the RL bending operation knob 18b.

The UD braking lever 18c is provided for braking an operation to rotate the UD bending operation knob 18a and configured to shift to a braking position at which rotation of the UD bending operation knob 18a is braked and an open position at which rotation of the UD bending operation knob 18a is not braked.

The RL braking grip 18d is provided for braking an operation to rotate the RL bending operation knob 18b and configured to shift to a braking position at which rotation of the RL braking grip 18d is braked and an open position at which the RL braking grip 18d is not braked.

The UD braking lever 18c and the RL braking grip 18d are configured to perform braking using, for example, frictional force and can control braking force at the braking positions. Thus, it is possible to restrict rotation of the UD braking lever 18c and the RL braking grip 18d when the UD braking lever 18c and the RL braking grip 18d are moved to the braking positions. In addition, it is possible to finely adjust rotational positions of the UD braking lever 18c and the RL braking grip 18d under exertion of braking force by slightly shifting the rotational positions.

A universal cable 17 is extended from a side part of the operation portion 12 on the proximal end side. An endoscope connector 17a is provided at an extension end of the universal cable 17. When the endoscope connector 17a is connected to a non-illustrated external instrument (such as a processor or a light source device), power source, a drive signal, illumination light, and the like are supplied to the mother endoscope 10 and a video picked up by the mother endoscope 10 is processed by the external instrument.

<Description of Baby Endoscope 20>

Subsequently, the baby endoscope 20 as an endoscope (cholangioscope) according to the present embodiment will be described below with reference to FIGS. 2 to 7 in addition to FIG. 1.

Figure 2:
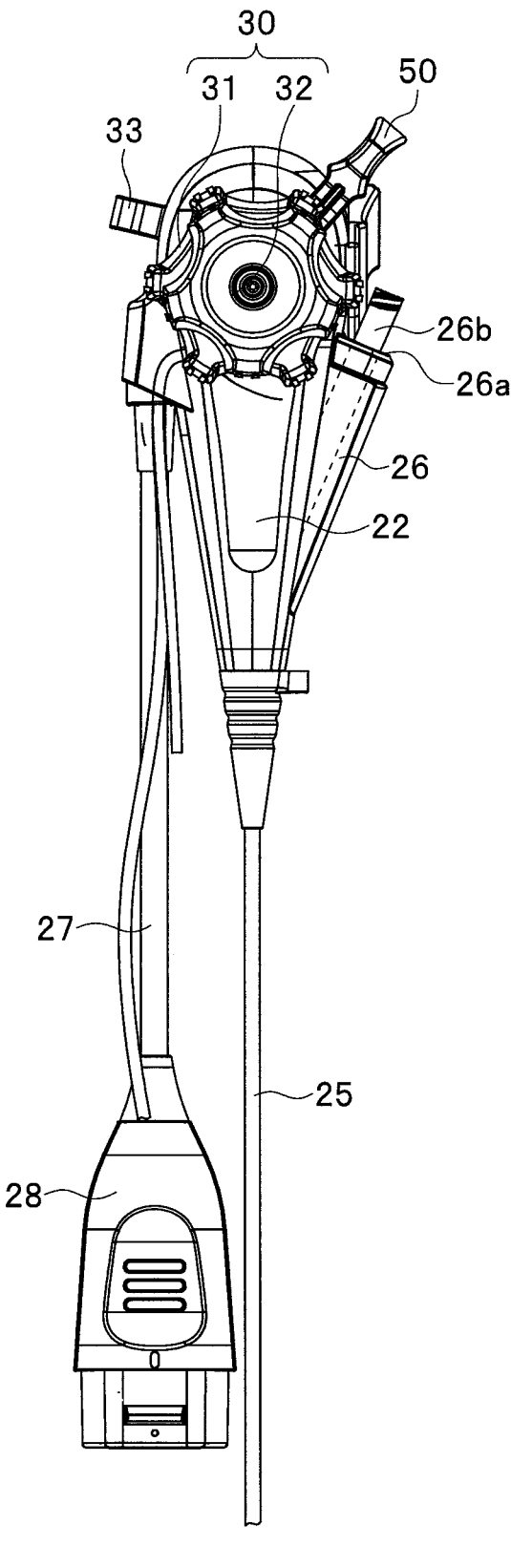
FIG. 2 is a front view illustrating an appearance of the baby endoscope according to the first embodiment.
Figure 3:
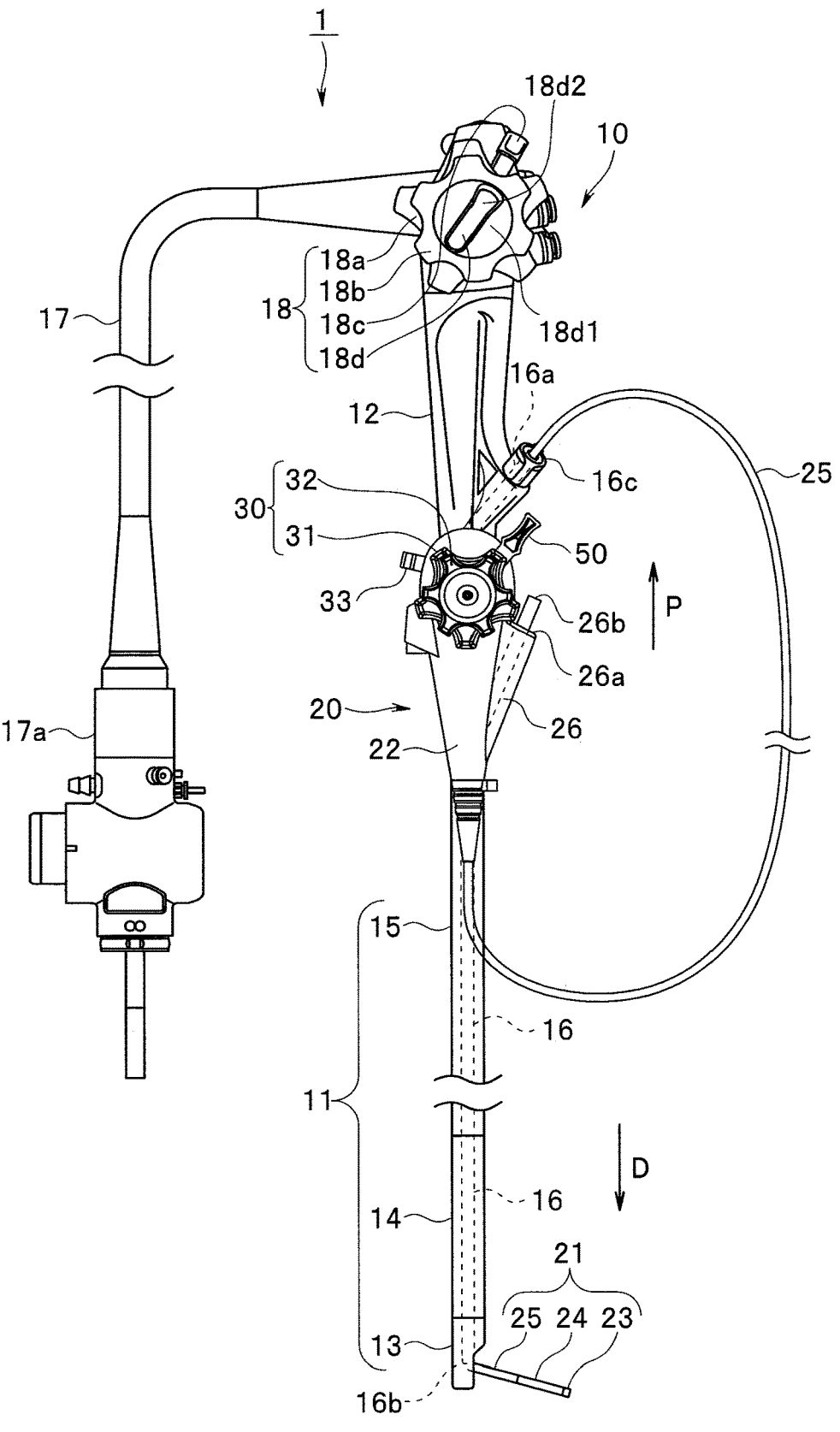
FIG. 3 is an exterior diagram illustrating a state in which the baby endoscope according to the first embodiment is mounted on the mother endoscope.

FIG. 2 is a front view illustrating an appearance of the baby endoscope according to the first embodiment, and FIG. 3 is an exterior diagram illustrating a state in which the baby endoscope according to the first embodiment is mounted on the mother endoscope.

As illustrated in FIGS. 1 and 2, the baby endoscope 20 includes the insertion portion 21 having an elongated shape that allows insertion into the treatment instrument insertion channel 16 of the mother endoscope 10, and an operation portion 22 continuously provided on the proximal end side of the insertion portion 21. Various operation members necessary for operating the baby endoscope 20 are disposed at the operation portion 22.

The insertion portion 21 includes a rigid distal end portion 23 provided on the distal end side, a bending portion 24 that is freely bendable and provided at a rear end of the distal end portion 23, and an elongated flexible tube portion 25 provided at a rear end of the bending portion 24.

Although not illustrated, for example, an LED light source configured to generate illumination light (or having a configuration in which illumination light from a light source device is transmitted through a light guide bundle), an illumination optical system configured to emit the generated illumination light, and an image pickup module in which an objective optical system and an image pickup device are built are disposed at the distal end portion 23 of the insertion portion 21. Note that, in the present embodiment, the image pickup device incorporated in the baby endoscope 20 is configured as a solid image pickup device such as a CCD image sensor or a CMOS image sensor.

The bending portion 24 of the insertion portion 21 is bendable in all directions about the insertion axis, including the up-down direction (U/D direction) as a first axial direction and the right-left direction (R/L direction) as a second axial direction.

The flexible tube portion 25 of the insertion portion 21 is configured as a flexible tubal member. Inside the flexible tube portion 25, a treatment instrument insertion channel 26 is formed, and in addition, for example, a predetermined image pickup cable, an electric power line for the LED light source, and an air-water feeding tube are disposed.

Two kinds of angle wires for bending the bending portion 24 (a first angle wire for bending the bending portion 24 in the up-down direction (U/D direction) and a second angle wire for bending the bending portion 24 in the right-left direction (R/L direction)) are extended in the flexible tube portion 25.

The treatment instrument insertion channel 26 is a treatment instrument insertion channel extending from the distal end portion 23 of the insertion portion 21 to the operation portion 22. The treatment instrument insertion channel 26 has a proximal end side opening 26a at the operation portion 22 and has a non-illustrated distal end side opening at the distal end portion 23 of the insertion portion 21. For example, a pipe sleeve 26b is provided at the proximal end side opening 26a of the operation portion 22.

A treatment instrument and the like can be inserted into the treatment instrument insertion channel 26 through the pipe sleeve 26b. The treatment instrument insertion channel 26 can be used to inject contrast dye and the like.

A bending operation handle portion 30 for an operation to bend the bending portion 24, a lock lever 50 for locking a bending state of the bending portion 24, and a fixation band hook 33 for locking a fixation band for mounting the baby endoscope 20 on the mother endoscope 10 are provided on the proximal end side of the operation portion 22.

In the present embodiment, the bending operation handle portion 30 includes a UD bending operation handle 31 and an RL bending operation handle 32. The UD bending operation handle 31, the RL bending operation handle 32, and the lock lever 50 are rotation operation members configured to be coaxially rotatable. Note that effects of the fixation band hook 33 will be described later.

Although described later in detail, the UD bending operation handle 31 is a bending operation member for an operation to bend the bending portion 24 in the up-down direction (U/D direction) as the first axial direction. Although not illustrated in FIG. 2, the UD bending operation handle 31 is coupled to a first pulley 41 connected to the first angle wire for an operation to bend the bending portion 24 in the up-down direction (U/D direction) inside the operation portion 22 (refer to FIG. 7).

The RL bending operation handle 32 is a bending operation member for an operation to bend the bending portion 24 in the right-left direction (R/L direction) as the second axial direction. Although not illustrated in FIG. 2, the RL bending operation handle 32 is coupled to a second pulley 42 connected to the second angle wire for an operation to bend the bending portion 24 in the right-left direction (R/L direction) inside the operation portion 22 (refer to FIG. 7).

It is possible to perform an operation to bend the bending portion 24 in all directions about the insertion axis as described above by combining bending in the up-down direction (U/D direction) through the UD bending operation handle 31 and bending in the right-left direction (R/L direction) through the RL bending operation handle 32.

The lock lever 50 is provided for controlling an operation to rotate the first pulley 41 that acts in cooperation with the UD bending operation handle 31 and rotate the second pulley 42 that acts in cooperation with the RL bending operation handle 32, and is configured to shift to a restriction position (locked state) at which rotation is restricted and an open position (unlocked state) at which rotation is not restricted.

Note that configurations and effects of the UD bending operation handle 31, the RL bending operation handle 32, the lock lever 50, the first pulley 41, and the second pulley 42 will be described later in detail.

As illustrated in FIG. 2, a universal cable 27 is extended from the proximal end side of the operation portion 22. The universal cable 27 incorporates an image pickup cable, an electric power line for an LED light source, and an air-water feeding tube. An endoscope connector 28 for connection to a non-illustrated external instrument (processor) is provided at an extension end of the universal cable 27. When the endoscope connector 28 is connected to the external instrument (processor), power source, a drive signal, and the like are supplied to the baby endoscope 20 and a video picked up by the baby endoscope 20 is processed by the external instrument.

FIG. 3 is an exterior diagram illustrating a state in which the baby endoscope according to the first embodiment is mounted on the mother endoscope.

Figure 14:
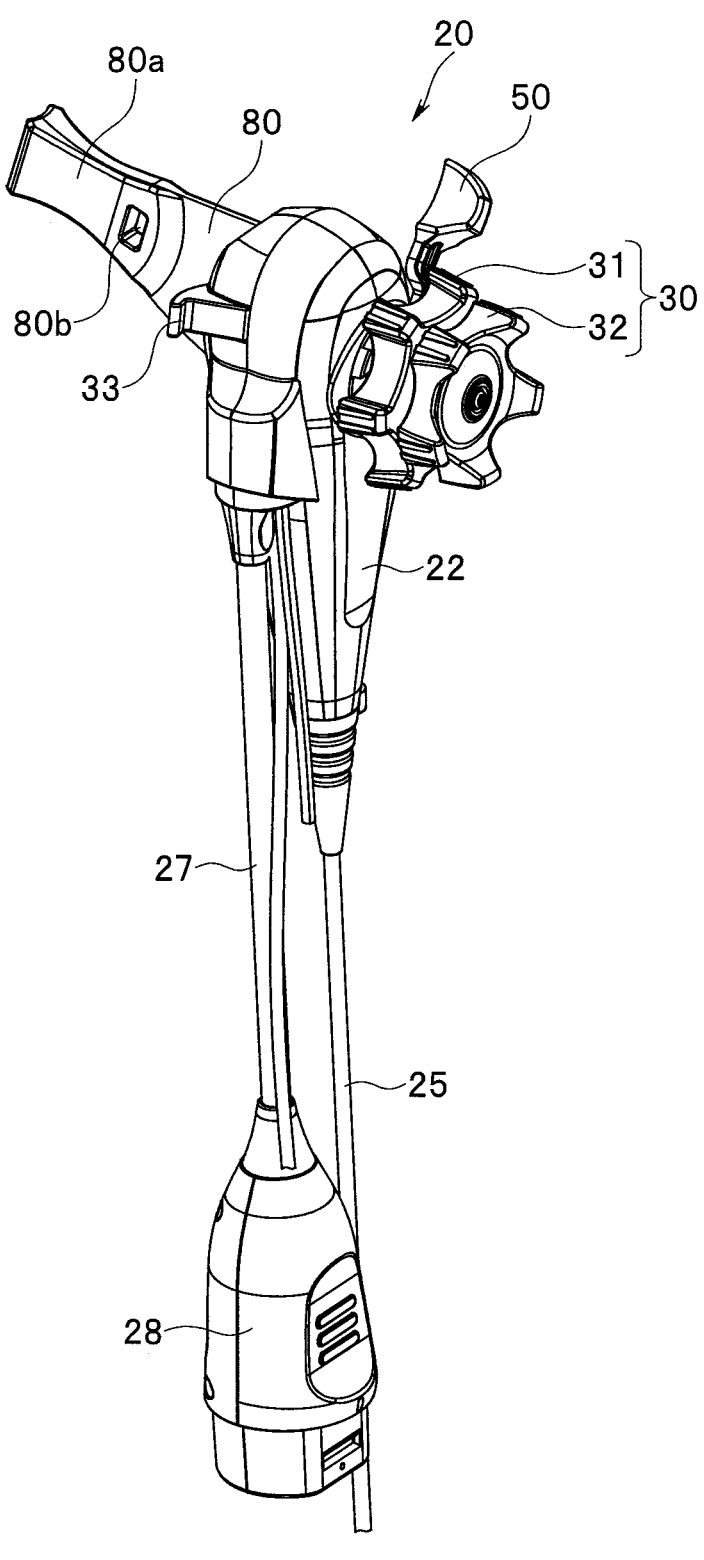
FIG. 14 is a perspective view illustrating an appearance of the baby endoscope according to the first embodiment together with a fixation band for fixation to the mother endoscope.
Figure 15:
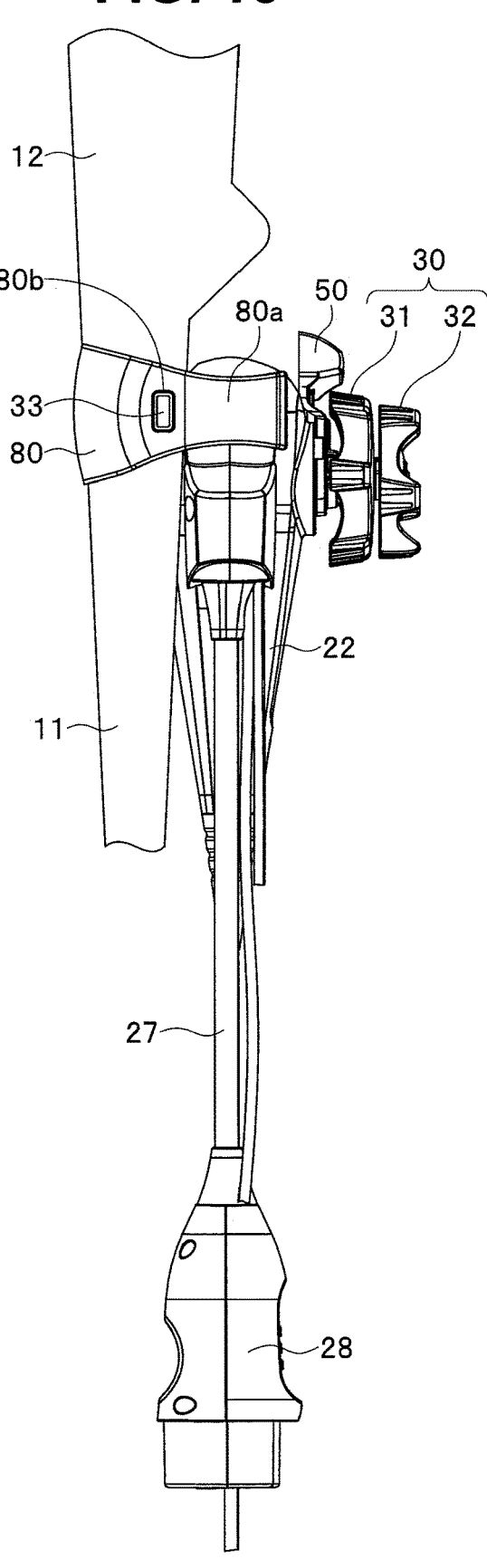
FIG. 15 is a side view of part of the operation portion of the baby endoscope according to the first embodiment and the mother endoscope, illustrating a state in which the baby endoscope is mounted on the mother endoscope.
Figure 16:
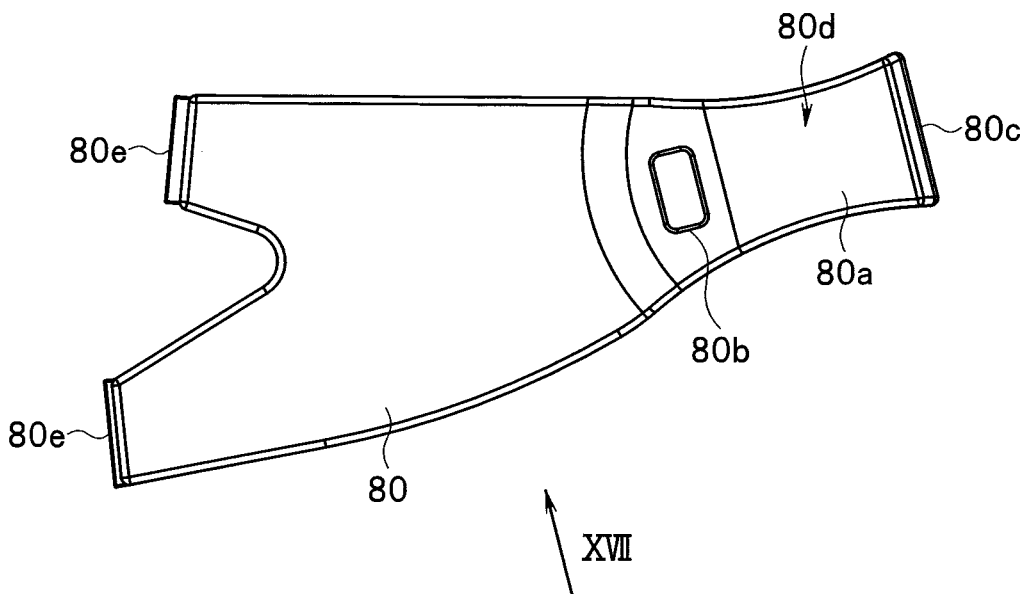
FIG. 16 is a perspective view illustrating the fixation band used when the baby endoscope according to the first embodiment is mounted on the mother endoscope.
Figure 17:
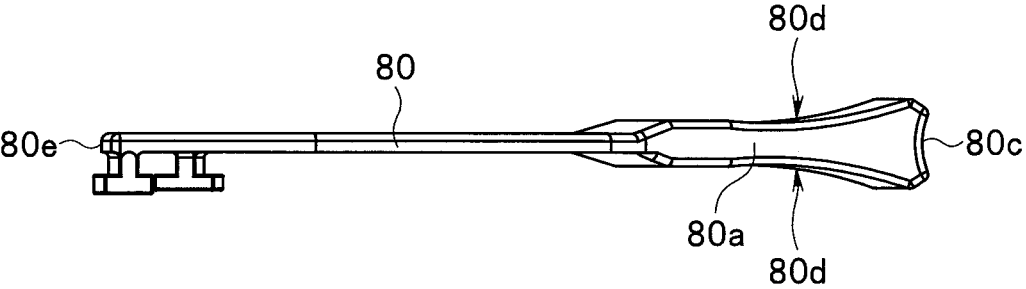
FIG. 17 is a side view illustrating the fixation band used when the baby endoscope according to the first embodiment is mounted on the mother endoscope.

In the present embodiment, the operation portion 22 of the baby endoscope 20 thus configured can be mounted on a lower part of the operation portion 12 of the mother endoscope 10 as illustrated in FIG. 3. For example, the operation portion 22 of the baby endoscope 20 is mounted on the lower part of the operation portion 12 of the mother endoscope 10 as illustrated in FIG. 15 by engaging a fixation band 80 as illustrated in FIGS. 14, 16, and 17 with the fixation band hook 33 of the operation portion 22 (note that illustration of the fixation band 80 is omitted in FIG. 3).

The above-described mounting of the baby endoscope 20 on the mother endoscope 10 through the fixation band 80 will be described later.

<Bending Operation Mechanism in Operation Portion>

Subsequently, a configuration of a bending operation mechanism 35 disposed in the operation portion 22 of the baby endoscope 20 will be described below with reference to FIGS. 4 to 7.

Figure 4:
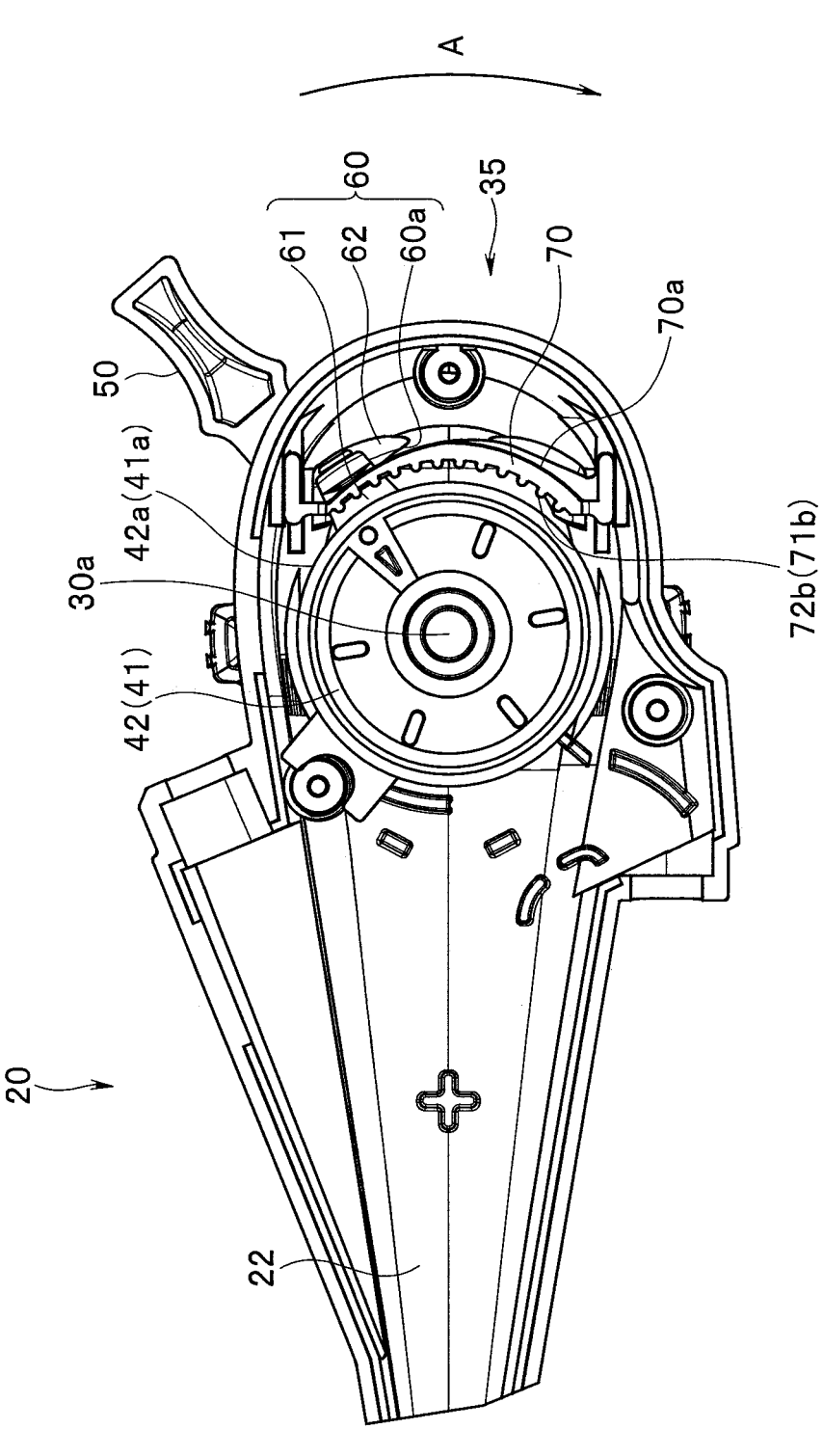
FIG. 4 is a diagram of inside of an operation portion of the baby endoscope according to the first embodiment when viewed from a back surface side, illustrating an unlocked state of a bending operation mechanism.
Figure 5:
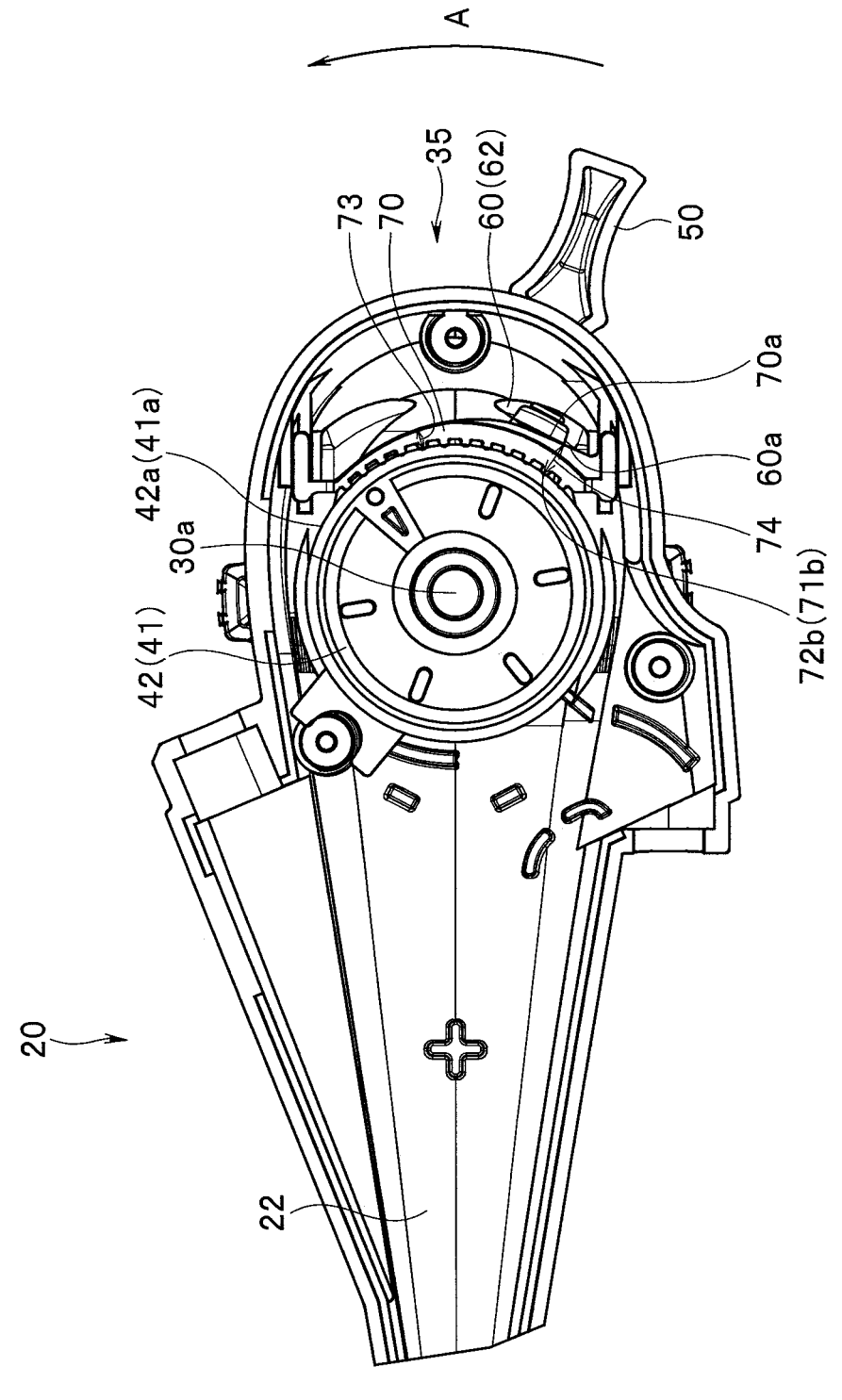
FIG. 5 is a diagram of inside of the operation portion of the baby endoscope according to the first embodiment when viewed from the back surface side, illustrating a locked state of the bending operation mechanism.
Figure 6:
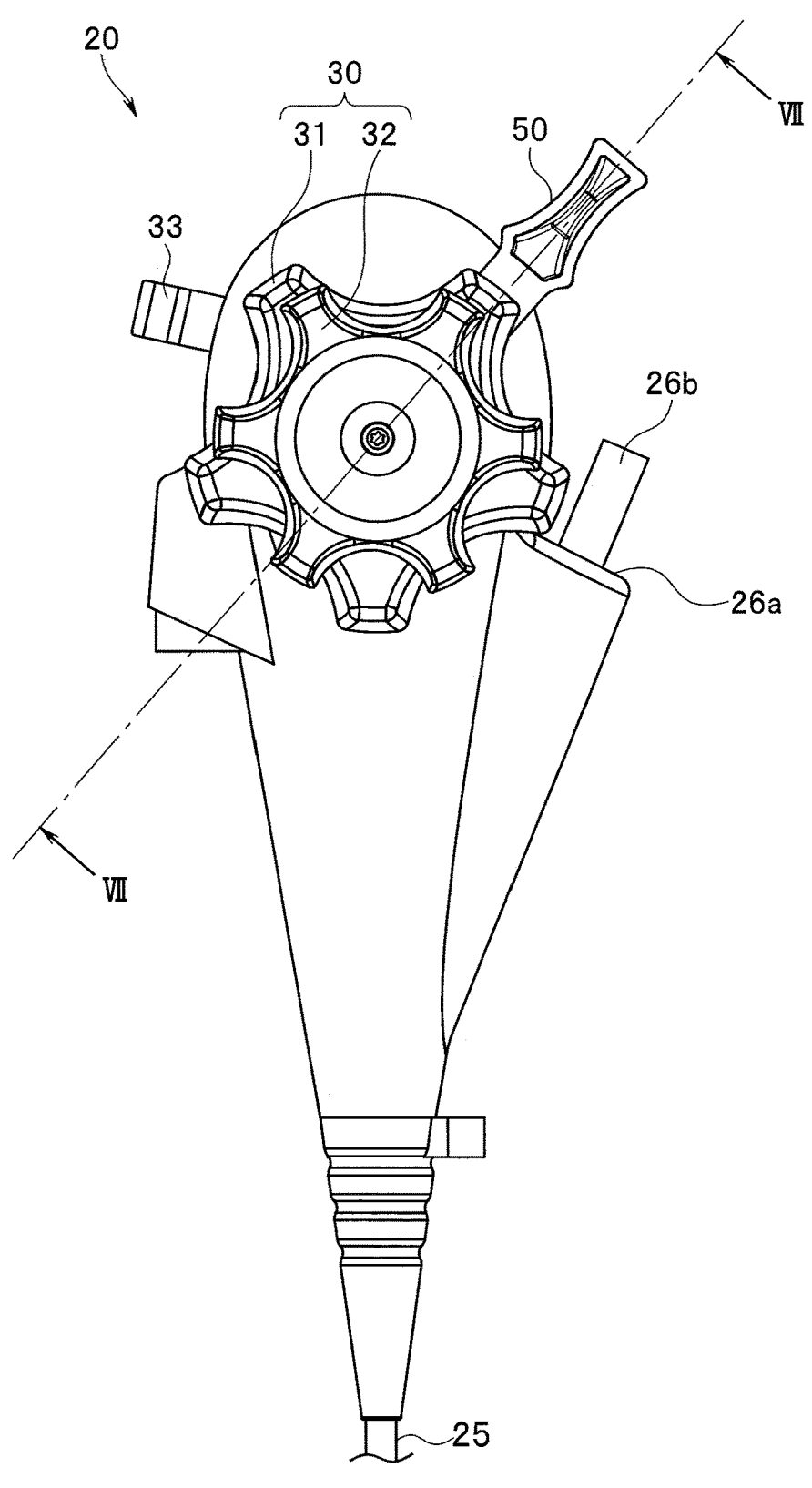
FIG. 6 is a front view of appearance of the operation portion of the baby endoscope according to the first embodiment viewed from a front surface side.
Figure 7:
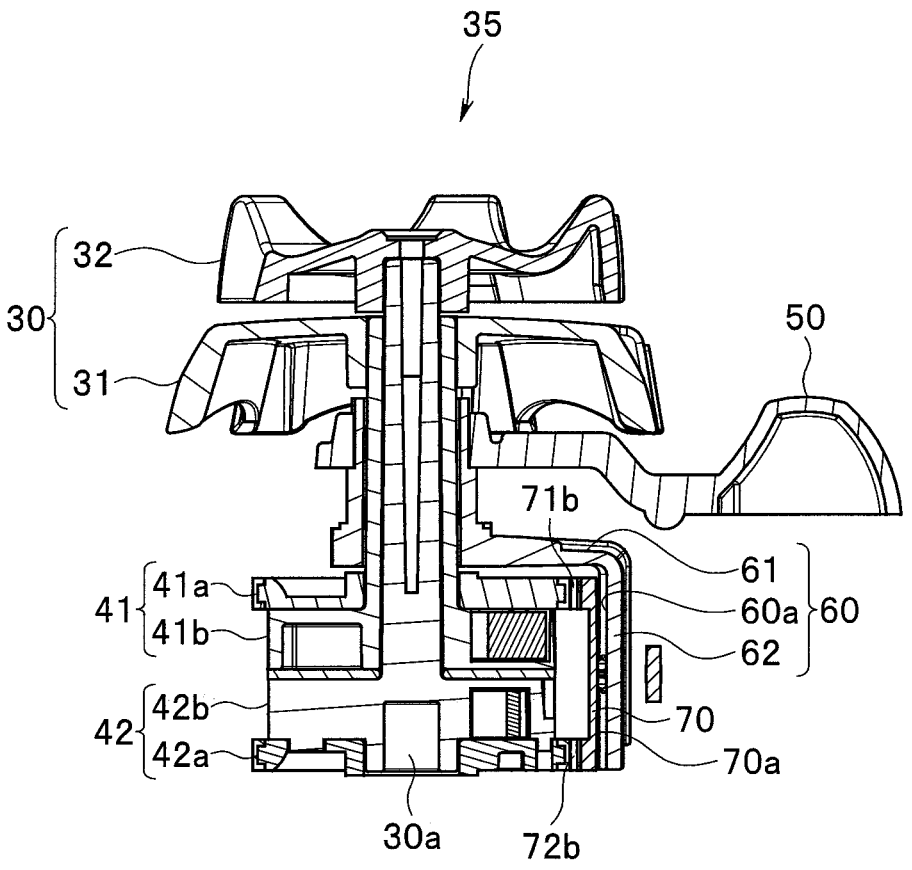
FIG. 7 is a main-part enlarged cross-sectional view illustrating the bending operation mechanism out of the operation portion of the baby endoscope according to the first embodiment.

FIGS. 4 and 5 are diagrams of the inside of the operation portion of the baby endoscope according to the first embodiment when viewed from a back surface side. FIG. 4 is a diagram illustrating an unlocked state of the bending operation mechanism, and FIG. 5 is a diagram illustrating a locked state of the bending operation mechanism. FIG. 6 is a front view of the appearance of the operation portion of the baby endoscope 20 viewed from a front surface side, and FIG. 7 is a main-part enlarged cross-sectional view illustrating the bending operation mechanism out of the operation portion.

The bending operation mechanism 35 in the present embodiment includes the UD bending operation handle 31 for an operation to bend the bending portion 24 in the first axial direction (U/D direction), and the RL bending operation handle 32 for an operation to bend the bending portion 24 in the second axial direction (R/L direction) orthogonal to the first axial direction. The bending operation mechanism 35 also includes the first pulley 41 that acts in cooperation with the UD bending operation handle 31, and the second pulley 42 that acts in cooperation with the RL bending operation handle 32. In addition, the bending operation mechanism 35 includes the lock lever 50 for controlling rotation of the first pulley 41 and the second pulley 42.

The bending operation mechanism 35 additionally includes a brake member 70 for restricting rotation of the first pulley 41 and the second pulley 42, and a cam member 60 that engages with the brake member 70 and shifts the brake member 70 in a radial direction of a rotational axis 30a.

The bending operation mechanism 35 having the above-described configuration will be described below in detail.

The UD bending operation handle 31 is a handle member having a substantially disk shape and rotatably supported about the rotational axis 30a and performs an operation to bend the bending portion 24 in the up-down direction (U/D direction) as the first axial direction. In other words, the bending portion 24 bends in the U direction (up direction) when the UD bending operation handle 31 is rotated in one direction, and the bending portion 24 bends in the D direction (down direction) when the UD bending operation handle 31 is rotated in the other direction.

The RL bending operation handle 32 is a handle member having a substantially disk shape on an upper surface that is coaxial with the UD bending operation handle 31, and rotatably supported about the rotational axis 30a. The RL bending operation handle 32 performs, independently from the UD bending operation handle 31, an operation to bend the bending portion 24 in the right-left direction (R/L direction) as the second axial direction orthogonal to the first axial direction. In other words, the bending portion 24 bends in the R direction (right direction) when the RL bending operation handle 32 is rotated in one direction, and the bending portion 24 bends in the L direction (left direction) when the RL bending operation handle 32 is rotated in the other direction.

It is possible to perform an operation to bend the bending portion 24 in all directions about the insertion axis as described above by combining bending in the up-down direction (U/D direction) through the UD bending operation handle 31 and bending in the right-left direction (R/L direction) through the RL bending operation handle 32.

The first pulley 41 connected to the first angle wire for an operation to bend the bending portion 24 in the first axial direction (U/D direction) and the second pulley 42 connected to the second angle wire for an operation to bend the bending portion 24 in the second axial direction (R/L direction) orthogonal to the first axial direction are disposed inside the operation portion 22 of the baby endoscope 20 (refer to FIG. 7).

Note that FIGS. 4 and 5 are diagrams of the inside of the operation portion 22 of the baby endoscope 20 when viewed from the back surface side, illustrating a state in which the second pulley 42 is exposed, but the first pulley 41 is disposed behind the second pulley 42 with respect to the sheet.

The first pulley 41 is a wire pulling member for the first angle wire and includes a wire connection surface 41b that has a predetermined radius and to which the first angle wire is connected and an outer peripheral surface 41a having a radius larger than the radius of the wire connection surface 41b (refer to FIG. 7). The outer peripheral surface 41a rotates integrally with the wire connection surface 41b and engages with the above-described brake member 70 under a predetermined condition.

The first pulley 41 is coupled to the UD bending operation handle 31 and supported to rotate about the rotational axis of the UD bending operation handle 31 along with rotation of the UD bending operation handle 31. In accordance with a rotational operation of the UD bending operation handle 31, the wire connection surface 41b of the first pulley 41 rotates, the first angle wire is pulled, and the bending portion 24 bends in the first axial direction (U/D direction).

The second pulley 42 is a wire pulling member for the second angle wire and includes a wire connection surface 42b that has a predetermined radius and to which the second angle wire is connected and an outer peripheral surface 42a having a radius (equal to the radius of the outer peripheral surface 41a) larger than the radius of the wire connection surface 42b (refer to FIG. 7). The outer peripheral surface 42a rotates integrally with the wire connection surface 42b and engages with the above-described brake member 70 under a predetermined condition.

The second pulley 42 is coupled to the RL bending operation handle 32 and supported to rotate about the rotational axis of the RL bending operation handle 32 along with rotation of the RL bending operation handle 32. In accordance with a rotational operation of the RL bending operation handle 32, the wire connection surface 42b of the second pulley 42 rotates, the second angle wire is pulled, and the bending portion 24 bends in the second axial direction (R/L direction).

The lock lever 50 is supported to be coaxially rotatable with the UD bending operation handle 31 and the RL bending operation handle 32 described above on the proximal end side of the operation portion 22 (refer to "A" in FIGS. 4 and 5). Specifically, the lock lever 50 is supported to be rotatable, independently from the UD bending operation handle 31 and the RL bending operation handle 32, on a first arc having a predetermined radius and having an axis center at the rotational axis 30a.

The lock lever 50 is provided for controlling rotation of the first pulley 41 that acts in cooperation with the UD bending operation handle 31 and the second pulley 42 that acts in cooperation with the RL bending operation handle 32, and is configured to shift to an unlocked state position (position illustrated in FIG. 4) at which rotation of the first pulley 41 and the second pulley 42 is not restricted and a locked state position (position illustrated in FIG. 5) at which rotation of the first pulley 41 and the second pulley 42 is restricted.

The cam member 60 includes an arm portion 61 configured to rotate integrally with the above-described rotation of the lock lever 50, and a cam portion 62 formed at a distal end portion of the arm portion 61.

The arm portion 61 couples to a proximal end portion of the lock lever 50 at a proximal end portion of the arm portion 61, integrates with the lock lever 50, and forms an arm extending from the rotational axis 30a outward in the radial direction.

The cam portion 62 includes a plate part at the distal end portion of the arm portion 61 extending from the rotational axis 30a outward in the radial direction, the plate part being bent in a direction parallel to an axial direction of the rotational axis 30a. A cam surface 60a facing a center of the rotational axis 30a is formed at the bent plate part.

The cam portion 62 is disposed to be movable, inside a case of the operation portion 22, on a second arc having an axis center at the rotational axis 30a (and having a radius smaller than the radius of the first arc). Note that the second arc is positioned outside the outer peripheral surface 41a of the first pulley 41 and the outer peripheral surface 42a of the second pulley 42 in the radial direction of the rotational axis 30a.

As described above, the cam portion 62 includes the cam surface 60*a* facing the center of the rotational axis 30*a* and moves on the second arc having an axis center at the rotational axis 30*a* so that the cam surface 60*a* constantly faces the rotational axis 30*a* along with the above-described rotation of the lock lever 50 (rotation on the first arc having an axis center at the rotational axis 30*a*).

A sectional shape of the brake member 70 along a plane orthogonal to the rotational axis 30*a* is formed of a bending plate member having a substantially partial arc shape and having an inner surface facing the rotational axis 30*a*. The brake member 70 is disposed between the outer peripheral surface 41*a* of the first pulley 41 (and the outer peripheral surface 42*a* of the second pulley 42) and the cam surface 60*a* of the cam portion 62 of the cam member 60.

Note that the brake member 70 is restricted from moving in a circumferential direction of an arc about the rotational axis 30*a* but is disposed to be movable in a direction in which the inner surface moves toward the rotational axis 30*a* or a direction in which the inner surface moves away from the rotational axis 30*a*, in other words, in the radial direction.

The brake member 70 includes, outside the above-described arc, a cam follower surface 70*a* capable of sliding relative to the cam surface 60*a* of the cam member 60 (cam portion 62). The brake member 70 also includes, inside the above-described arc, a contact surface 71*b* capable of contacting the outer peripheral surface 41*a* of the first pulley 41, and a contact surface 72*b* capable of contacting the outer peripheral surface 42*a* of the second pulley 42.

Note that the above-described cam follower surface 70*a* is a first surface of the brake member 70, the first surface being capable of sliding relative to the cam surface 60*a*. The contact surface 71*b* is a second surface of the brake member 70, the second surface being capable of contacting the outer peripheral surface 41*a* of the first pulley 41 and the outer peripheral surface 42*a* of the second pulley 42.

The contact surface 71*b* and the contact surface 72*b* of the brake member 70 are positioned separately from the outer peripheral surface 41*a* of the first pulley 41 and the outer peripheral surface 42*a* of the second pulley 42 when the lock lever 50 is positioned in the unlocked state illustrated in FIG. 4 (state in which rotation of the first pulley 41 and the second pulley 42 is not restricted).

Note that, in the present embodiment, the contact surface 71*b* and the contact surface 72*b* are positioned separately from the outer peripheral surface 41*a* and the outer peripheral surface 42*a*, respectively, when the lock lever 50 is positioned in the unlocked state. However, the present invention is not limited to this configuration, the contact surface 71*b* and the contact surface 72*b* may contact the outer peripheral surface 41*a* and the outer peripheral surface 42*a* as long as no frictional force that restricts rotation of the first pulley 41 and the second pulley 42 is generated.

Although described later in detail, when the lock lever 50 is positioned in the locked state illustrated in FIG. 5 (state in which rotation of the first pulley 41 and the second pulley 42 is restricted), the contact surface 71*b* and the contact surface 72*b* of the brake member 70 move to positions where the contact surfaces contact the outer peripheral surface 41*a* and the outer peripheral surface 42*a*, respectively, and restrict rotation of the first pulley 41 and the second pulley 42 with predetermined frictional force.

In the present embodiment, the contact surface 71*b* and the contact surface 72*b* of the brake member 70 are formed to generate predetermined frictional force at a level sufficient to restrict rotation of the first pulley 41 and the second pulley 42 when contacting the outer peripheral surfaces of the pulleys facing the respective contact surfaces. Note that a mechanism configured to generate click sensing may be provided at the lock lever 50 to inform that the predetermined frictional force is generated and rotation of the first pulley 41 and the second pulley 42 is restricted.

In the first embodiment, claw portions arranged at a predetermined pitch are formed on each of the contact surface 71*b* facing the outer peripheral surface 41*a* of the first pulley 41 and the contact surface 72*b* facing the outer peripheral surface 42*a* of the second pulley 42. It is set that, when the lock lever 50 is rotated to the locked state illustrated in FIG. 5, the contact surface 71*b* and the contact surface 72*b* contact the outer peripheral surface 41*a* and the outer peripheral surface 42*a*, respectively, due to effects of the cam member 60 and generate frictional force that can restrict rotation of the first pulley 41 and the second pulley 42.

In the present embodiment, the brake member 70 is formed so that a thickness in the radial direction (in other words, distance between the cam follower surface 70*a* and the contact surface 71*b* or the contact surface 72*b*) shifts in the circumferential direction. Specifically, as illustrated in FIG. 5, the brake member 70 includes a first cam follower portion 73 and a second cam follower portion 74, the first cam follower portion 73 including a part at which the distance between the cam follower surface 70*a* and the contact surface 71*b* or the contact surface 72*b* is equal to a first length, the second cam follower portion 74 including a part at which the distance is equal to a second length longer than the first length.

The cam follower surface 70*a* is formed with smooth shift from a part near the first cam follower portion 73 to a part near the second cam follower portion 74. As described above, it is set that the thickness of the second cam follower portion 74 of the brake member 70 in the radial direction is larger than the thickness of the first cam follower portion 73 in the radial direction. In the present embodiment, the cam follower surface 70*a* is disposed at a position of entering the second arc, on which the cam portion 62 moves, at the part near the second cam follower portion 74.

Since the brake member 70 includes the cam follower surface 70*a* having the above-described shape, the cam surface 60*a* gradually press the cam follower surface 70*a* toward the rotational axis 30*a* as the cam portion 62 reaches the part near the second cam follower portion 74 while moving on the second arc and sliding on the cam follower surface 70*a* along with rotation of the lock lever 50.

In other words, the cam follower surface 70*a* of the brake member 70 is pressed toward the rotational axis 30*a* in accordance with movement of the cam surface 60*a* as the cam surface 60*a* of the cam portion 62 reaches the cam follower surface 70*a* of the part near the second cam follower portion 74 in accordance with movement of the cam portion 62 on the second arc. In this case, the brake member 70 moves toward the rotational axis 30*a*, in other words, in the radial direction, and the contact surface 71*b* and the contact surface 72*b* of the brake member 70 move toward the outer peripheral surface 41*a* of the first pulley 41 and the outer peripheral surface 42*a* of the second pulley 42, respectively, and eventually contact the facing outer peripheral surfaces, respectively.

After contacting the facing outer peripheral surface 41*a* and the facing outer peripheral surface 42*a*, respectively, the contact surface 71*b* and the contact surface 72*b* of the brake member 70 press the outer peripheral surface 41*a* and the outer peripheral surface 42*a* due to effects of the cam follower surface 70a sliding on the cam surface 60a moving along with rotation of the lock lever 50.

Force of the pressing generates predetermined frictional force between the contact surface 71b and the outer peripheral surface 41a and between the contact surface 72b and the outer peripheral surface 42a, and rotation of the first pulley 41 and the second pulley 42 is restricted by the frictional force. Accordingly, rotation of the first pulley 41 and the second pulley 42 is restricted and the locked state is completed through an operation of the lock lever 50.

<Effects of Bending Operation Mechanism 35>

Subsequently, effects of the bending operation mechanism 35 thus configured will be described below.

Assume that the lock lever 50 is positioned, for example, in the unlocked state illustrated in FIG. 4. In this case, the cam surface 60a of the cam portion 62 is in contact with the cam follower surface 70a near the first cam follower portion 73 of the brake member 70.

Assume that an operator rotates the lock lever 50 in a direction "A" in the drawing to change the unlocked state (state illustrated in FIG. 4) to the locked state (state illustrated in FIG. 5). In this case, the lock lever 50 rotates on the first arc having an axis center at the rotational axis 30a from a position illustrated in FIG. 4 to a position illustrated in FIG. 5.

In accordance with rotation of the lock lever 50, the cam portion 62 of the cam member 60 moves on the second arc having an axis center at the rotational axis 30a, and the cam surface 60a of the cam portion 62 starts to slide on the cam follower surface 70a (the cam follower surface 70a starts to relatively slide on the cam surface 60a).

In this case, the cam surface 60a, which is initially in the unlocked state (state illustrated in FIG. 4) and in contact with the cam follower surface 70a near the first cam follower portion 73, starts to gradually slide toward the cam follower surface 70a near the second cam follower portion 74 in accordance with rotation of the lock lever 50.

As described above, in the present embodiment, the thickness of the second cam follower portion 74 of the brake member 70 in the radial direction is set to be larger than the thickness of the first cam follower portion 73 in the radial direction, and the cam follower surface 70a is disposed at the position of entering the second arc, on which the cam portion 62 moves, at the part near the second cam follower portion 74. Thus, the cam surface 60a gradually presses the cam follower surface 70a toward the rotational axis 30a as the cam portion 62 reaches the part near the second cam follower portion 74 while moving on the second arc and sliding on the cam follower surface 70a along with rotation of the lock lever 50.

As the cam follower surface 70a of the brake member 70 is pressed toward the rotational axis 30a by the cam surface 60a, the contact surface 71b and the contact surface 72b on an opposite side move toward the outer peripheral surfaces of the first pulley 41 and the second pulley 42 facing the respective contact surfaces and then contact the respective outer peripheral surfaces.

Thereafter, as the lock lever 50 is further rotated, the contact surface 71b and the contact surface 72b of the brake member 70 press the outer peripheral surface 41a and the outer peripheral surface 42a facing the respective contact surfaces. Then, force of the pressing generates predetermined frictional force between the contact surface 71b and the outer peripheral surface 41a and between the contact surface 72b and the outer peripheral surface 42a, and rotation of the first pulley 41 and the second pulley 42 is restricted by the frictional force.

When the lock lever 50 is rotated to the position in the locked state illustrated in FIG. 5, the locked state of the first pulley 41 and the second pulley 42 by the brake member 70 is completed.

As described above, in the endoscope incorporating the insertion-instrument bending operation mechanism according to the first embodiment, each pulley to which an angle wire for bending the bending portion is connected is pressed in the radial direction of the rotational axis by the brake member, which is disposed on the circumference of the pulley, to restrict rotation of the pulley. Thus, it is possible to reduce a thickness of the operation portion as compared to a configuration including a mechanism configured to press the pulley in a thrust direction, and it is possible to ensure favorable operability without size increase of the operation portion.

For example, when the insertion-instrument bending operation mechanism according to the first embodiment is employed as a baby endoscope in a mother-baby endoscope system and the baby endoscope is mounted on a mother endoscope, it is possible to reduce the thickness of the operation portion of the baby endoscope protruding from the mother endoscope. Thus, even when the operator operates the baby endoscope in this state, it is possible to ensure favorable operability without degradation of operability of the baby endoscope.

Modifications of First Embodiment

First Modification

Subsequently, a first modification of the insertion-instrument bending operation mechanism according to the first embodiment will be described below with reference to FIGS. 8 and 9.

Figure 8:
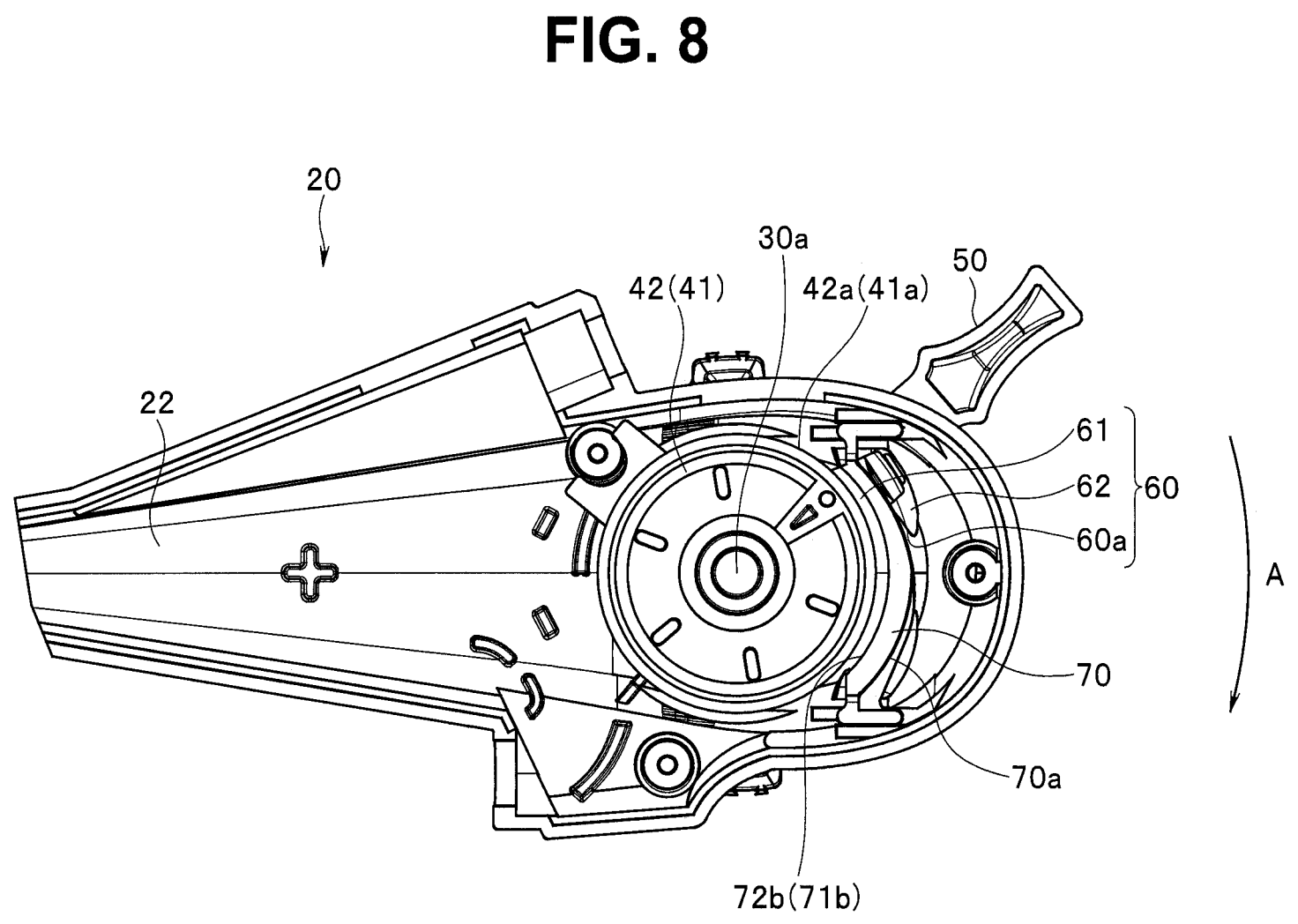
Figure 9:
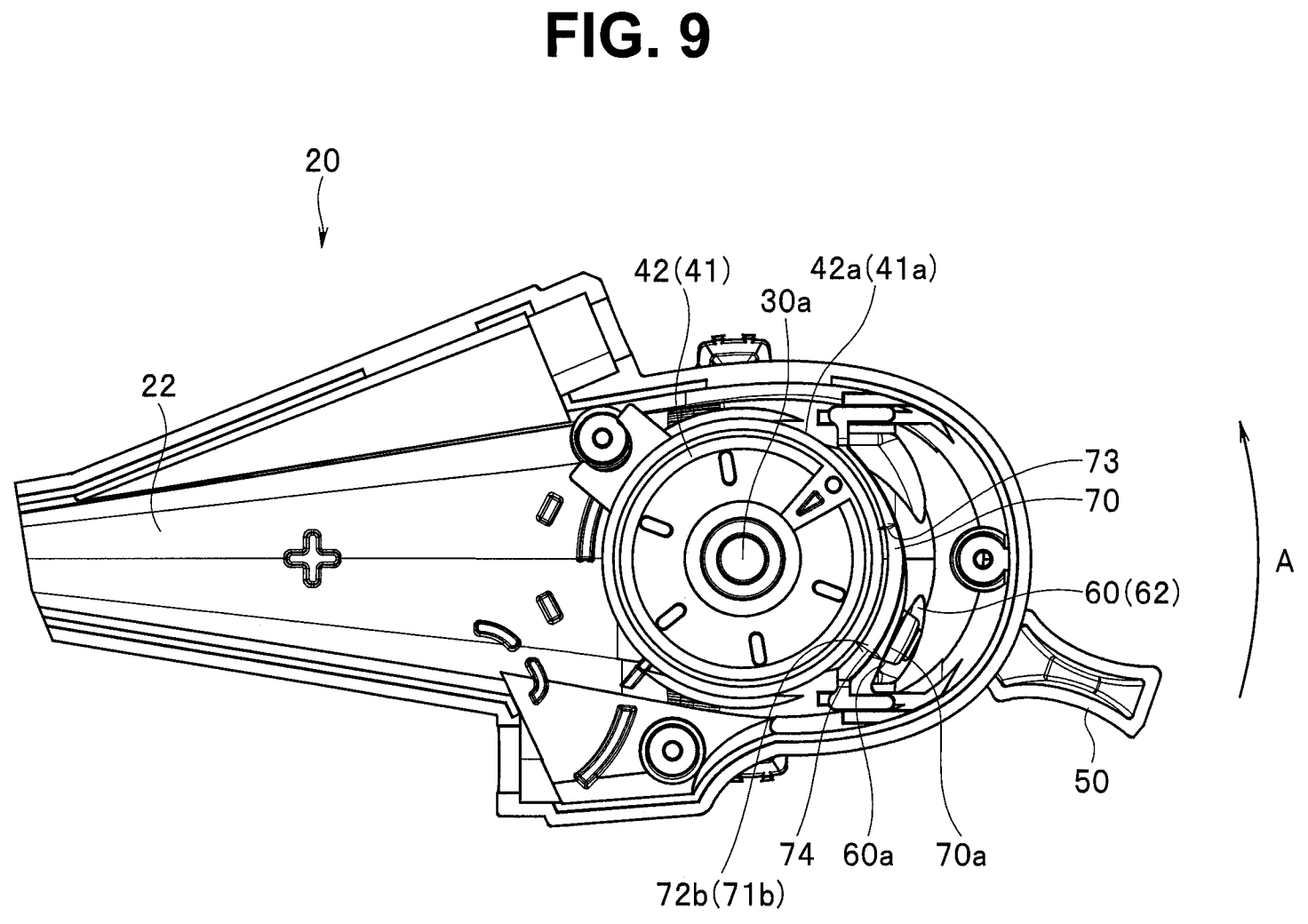

FIG. 8 is a diagram of the inside of the operation portion of the baby endoscope according to the first modification of the first embodiment when viewed from the back surface side, illustrating the unlocked state of the bending operation mechanism. FIG. 9 is a diagram of the inside of the operation portion of the baby endoscope according to the first modification of the first embodiment when viewed from the back surface side, illustrating the locked state of the bending operation mechanism.

In the first embodiment described above, the claw portions are formed on the contact surface 71b and the contact surface 72b in the brake member 70 for restricting rotation of the first pulley 41 and the second pulley 42, and predetermined frictional force is generated between the claw portions on the contact surfaces and the outer peripheral surfaces of the pulleys when the contact surface 71b and the contact surface 72b contact the outer peripheral surface 41a of the first pulley 41 and the outer peripheral surface 42a of the second pulley 42, respectively, and predetermined pressing force is applied.

In the first modification, the contact surface 71b and the contact surface 72b of the brake member 70 are formed of a material having a predetermined high friction coefficient in place of the above-described claw portions, and the outer peripheral surface 41a and the outer peripheral surface 42a facing the contact surface 71b and the contact surface 72b, respectively, are formed of the material having the predetermined high friction coefficient.

The friction coefficient of the material of the contact surfaces and the outer peripheral surfaces is a friction coefficient corresponding to frictional force with which rotation of the first pulley 41 and the second pulley 42 can be restricted when the contact surfaces contact the respective outer peripheral surfaces.

Note that, in the first modification, the contact surfaces and the outer peripheral surfaces are each formed of the material having the predetermined high friction coefficient, but any one of the contact surfaces and the outer peripheral surfaces may be formed of the material.

Instead of formation with the material having the high friction coefficient, for example, appropriate surface roughness may be provided or surface fabrication such as emboss fabrication may be provided as long as the friction coefficient as described above is obtained. Alternatively, a member having a high friction coefficient may be attached to the contact surfaces or the outer peripheral surfaces.

In the first modification as well, similarly to the first embodiment described above, it is possible to reduce the thickness of the operation portion, and it is possible to ensure favorable operability without size increase of the operation portion.

<Second Modification>

Subsequently, a second modification of the insertion-instrument bending operation mechanism according to the first embodiment will be described below with reference to FIGS. 10 and 11.

Figure 10:
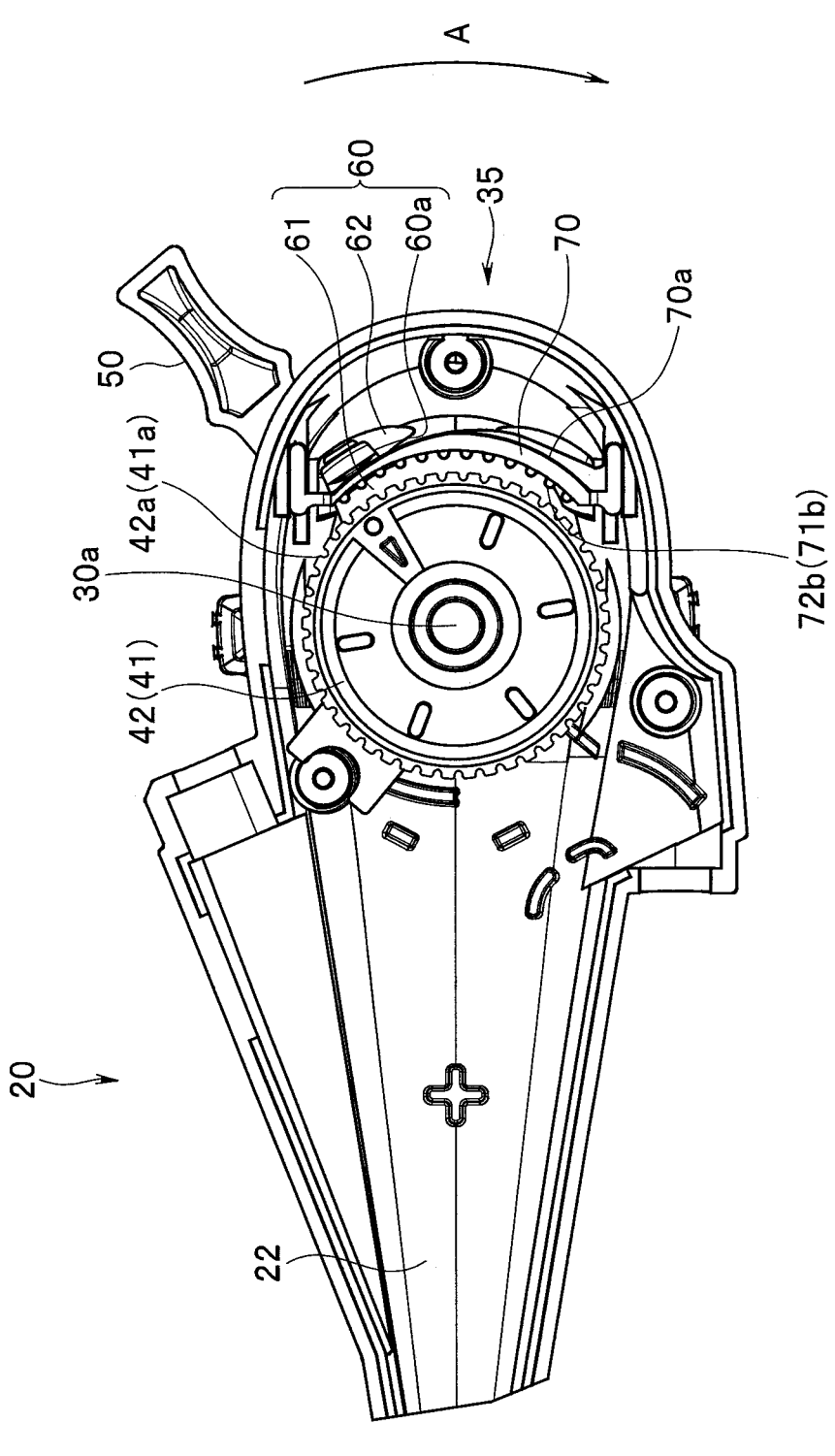
FIG. 10 is a diagram of an inside of the operation portion of a baby endoscope according to a second modification of the first embodiment when viewed from the back surface side, illustrating the unlocked state of the bending operation mechanism.

FIG. 10 is a diagram of the inside of the operation portion of the baby endoscope according to the second modification of the first embodiment when viewed from the back surface side, illustrating the unlocked state of the bending operation mechanism. FIG. 11 is a diagram of the inside of the operation portion of the baby endoscope according to the second modification of the first embodiment when viewed from the back surface side, illustrating the locked state of the bending operation mechanism.

In the first embodiment described above, the claw portions are formed on the contact surface 71b and the contact surface 72b in the brake member 70 for restricting rotation of the first pulley 41 and the second pulley 42, the contact surfaces contact the pulley outer peripheral surfaces facing the respective contact surfaces, and predetermined frictional force is generated between the claw portions on the contact surfaces and the outer peripheral surfaces of the pulleys when predetermined pressing force is applied.

Figure 11:
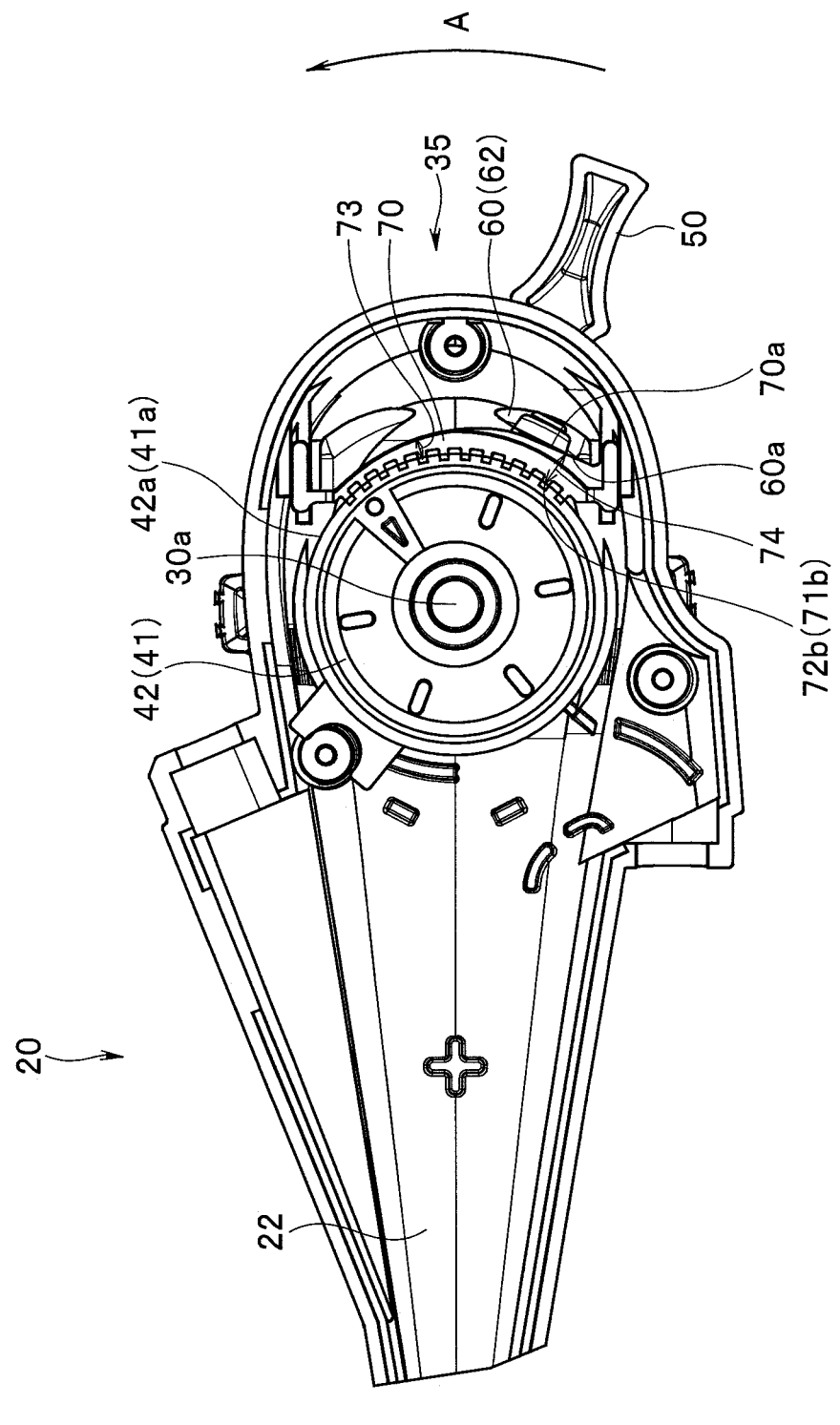
FIG. 11 is a diagram of an inside of the operation portion of the baby endoscope according to the second modification of the first embodiment when viewed from the back surface side, illustrating the locked state of the bending operation mechanism.

As illustrated in FIGS. 10 and 11, in the second modification, irregularity portions having a predetermined pitch are formed on the outer peripheral surface 41a of the first pulley 41 and the outer peripheral surface 42a of the second pulley 42, and irregularity portions that mesh with the irregularity portions are formed on the contact surface 71b and the contact surface 72b of the brake member 70, facing the outer peripheral surfaces.

In the second modification, the irregularity portions formed on the contact surfaces and the pulley outer peripheral surfaces mesh with each other (refer to FIG. 11) to reliably restrict rotation of the first pulley 41 and the second pulley 42 when the contact surface 71b and the contact surface 72b of the brake member 70 contact the outer peripheral surface 41a of the first pulley 41 and the outer peripheral surface 42a of the second pulley 42, respectively, and predetermined pressing force is applied.

Note that, in the second modification, the irregularity portions, which have the predetermined pitch, mesh with each other, and are formed on both the contact surfaces and the outer peripheral surfaces, may have various shapes, for example, a saw teeth shape.

In the second modification as well, similarly to the first embodiment described above, it is possible to reduce the thickness of the operation portion, and it is possible to ensure favorable operability without size increase of the operation portion.

Second Embodiment

Subsequently, an endoscope incorporating an insertion-instrument bending operation mechanism according to a second embodiment of the present invention will be described below. Note that, similarly to the first embodiment, the endoscope according to the second embodiment is assumed to be what is called a cholangioscope and assumed to be a baby endoscope applied to a mother endoscope in a mother-baby endoscope system.

The insertion-instrument bending operation mechanism according to the first embodiment described above includes the first angle wire for an operation to bend the bending portion 24 in the U/D direction, the first pulley 41 connected to the wire, the second angle wire for an operation to bend the bending portion 24 in the R/L direction, the second pulley 42 connected to the wire, and the UD bending operation handle 31 and the RL bending operation handle 32 connected to the first pulley 41 and the second pulley 42, respectively, and also includes the lock lever 50, the cam member 60, the brake member 70, and the like that collectively set the first pulley 41 and the second pulley 42 to the locked state.

In this manner, in the insertion-instrument bending operation mechanism according to the first embodiment, rotation of the first pulley 41 and the second pulley 42 corresponding to different axial directions, respectively, and independent from each other are restricted (locked) through one lever operation. However, the bending operation mechanism of the present application invention is also applicable to a bending operation in one axial direction among bending operations in a plurality of axial directions. Alternatively, the bending operation mechanism of the present application invention is also applicable to an endoscope on which a bending operation is performed only in one axial direction.

In the insertion-instrument bending operation mechanism according to the second embodiment of the present invention, the brake member 70 as described in the first embodiment restricts rotation of a pulley to which an angle wire for a bending operation in one axial direction among bending operations in a plurality of axial directions is connected. Specifically, the brake member 70 restricts only rotation of the first pulley 41 connected to the first angle wire for an operation to bend the bending portion 24 in the U/D direction.

In this manner, the insertion-instrument bending operation mechanism according to the second embodiment has a basic configuration same as in the first embodiment and is different from the first embodiment in that the brake member 70 includes, as a contact surface facing a pulley, only the contact surface 71b facing the outer peripheral surface 41a of the first pulley 41 and restricts only rotation of the first pulley 41. The other configuration is the same as in the first embodiment, and thus only the difference will be described below.

<Bending Operation Mechanism in Operation Portion in Second Embodiment>

Similarly to the first embodiment, the insertion-instrument bending operation mechanism according to the second embodiment will be described below with reference to FIGS. 4 to 7.

Similarly to the first embodiment, the bending operation mechanism in the second embodiment includes the UD bending operation handle 31 for an operation to bend the bending portion 24 in the first axial direction (U/D direction), and the RL bending operation handle 32 for an operation to bend the bending portion 24 in the second axial direction (R/L direction) orthogonal to the first axial direction. The bending operation mechanism also includes the first pulley 41 that acts in cooperation with the UD bending operation handle 31, and the second pulley 42 that acts in cooperation with the RL bending operation handle 32. The bending operation mechanism further includes the lock lever 50 for controlling rotation of the first pulley 41 and the second pulley 42. The bending operation mechanism additionally includes the brake member 70 for restricting rotation of the first pulley 41 and the second pulley 42, and the cam member 60 that engages with the brake member 70 and shifts the brake member 70 in the radial direction of the rotational axis 30a.

The lock lever 50 in the second embodiment is provided for controlling only rotation of the first pulley 41 that acts in cooperation with the UD bending operation handle 31, and configured to shift to an unlocked state position at which rotation of the first pulley 41 is not restricted and a locked state position at which rotation of the first pulley 41 is restricted.

The brake member 70 in the second embodiment includes the cam follower surface 70a capable of sliding relative to the cam surface 60a of the cam portion 62 and includes only the contact surface 71b capable of contacting the outer peripheral surface 41a of the first pulley 41, but does not include the contact surface 72b as in the first embodiment. When the lock lever 50 is positioned in the unlocked state, the contact surface 71b of the brake member 70 in the second embodiment is positioned separately from the outer peripheral surface 42a on the outer peripheral surface 41a of the first pulley 41.

When the lock lever 50 is positioned in the locked state, the contact surface 71b of the brake member 70 moves to a position where the contact surface 71b contacts the outer peripheral surface 41a, and restricts rotation of the first pulley 41 with predetermined frictional force.

In the second embodiment as well, the brake member 70 includes the first cam follower portion 73 and the second cam follower portion 74, the first cam follower portion 73 including a part at which the distance between the cam follower surface 70a and the contact surface 71b is equal to a first length, the second cam follower portion 74 including a part at which the distance is equal to a second length longer than the first length. The cam follower surface 70a is formed with smooth shift from a part near the first cam follower portion 73 to a part near the second cam follower portion 74.

As described above, the thickness of the second cam follower portion 74 of the brake member 70 in the radial direction is set to be larger than the thickness of the first cam follower portion 73 in the radial direction, and in the present embodiment as well, the cam follower surface 70a is disposed at the position of entering the second arc, on which the cam portion 62 moves, at the part near the second cam follower portion 74.

Similarly to the first embodiment, the cam follower surface 70a of the brake member 70 moves in the radial direction of the rotational axis 30a while being pressed by the cam surface 60a of the cam portion 62 moving in accordance with rotation of the lock lever 50. Accordingly, the contact surface 71b of the brake member 70 contacts the outer peripheral surface 41a of the first pulley 41, thereby restricting rotation of the first pulley 41.

As described above, similarly to the first embodiment, in the endoscope incorporating the insertion-instrument bending operation mechanism according to the second embodiment, a pulley to which an angle wire for bending the bending portion is connected is pressed in the radial direction of the rotational axis by the brake member, which is disposed on the circumference of the pulley, to restrict rotation of the pulley. Thus, it is possible to reduce the thickness of the operation portion as compared to a configuration including a mechanism configured to press the pulley in the thrust direction, and it is possible to ensure favorable operability without size increase of the operation portion.

Note that, in the second embodiment, only rotation of the first pulley 41 connected to the first angle wire for an operation to bend the bending portion 24 in the U/D direction is restricted. However, the present invention is not limited to this configuration, and only rotation of the second pulley 42 connected to the second angle wire for an operation to bend the bending portion 24 in the R/L direction may be restricted.

As described above, a technical idea of the bending operation mechanism of the present application invention is also applicable to an endoscope that allows a bending operation only in one axial direction, for example, an endoscope only including the first angle wire for an operation to bend the bending portion 24 in the UD direction, the first pulley 41 connected to the wire, and the UD bending operation handle 31 connected to the first pulley 41.

Third Embodiment

Subsequently, an endoscope incorporating an insertion-instrument bending operation mechanism according to a third embodiment of the present invention will be described below. Note that, similarly to the first embodiment, the endoscope according to the third embodiment is assumed to be what is called a cholangioscope and assumed to be a baby endoscope applied to a mother endoscope in a mother-baby endoscope system.

Similarly to the first embodiment, the endoscope incorporating the insertion-instrument bending operation mechanism according to the third embodiment allows bending operations of the bending portion in a plurality of different axial directions (in the present embodiment, two axial directions). In addition, the endoscope includes two pulleys corresponding to the two axial directions and also includes a lock lever for collectively locking the two pulleys, a cam member including a cam surface, and a brake member including a cam follower surface and a contact surface. However, the endoscope is different from the endoscope of the first embodiment in a relation between the cam surface and the cam follower surface. The other configuration is the same as in the first embodiment, and thus only the difference will be described below.

<Bending Operation Mechanism in Operation Portion According to Third Embodiment>

Subsequently, a configuration of a bending operation mechanism 135 disposed in the operation portion of a baby endoscope 120 according to the third embodiment will be described below with reference to FIGS. 12 and 13.

Figure 12:
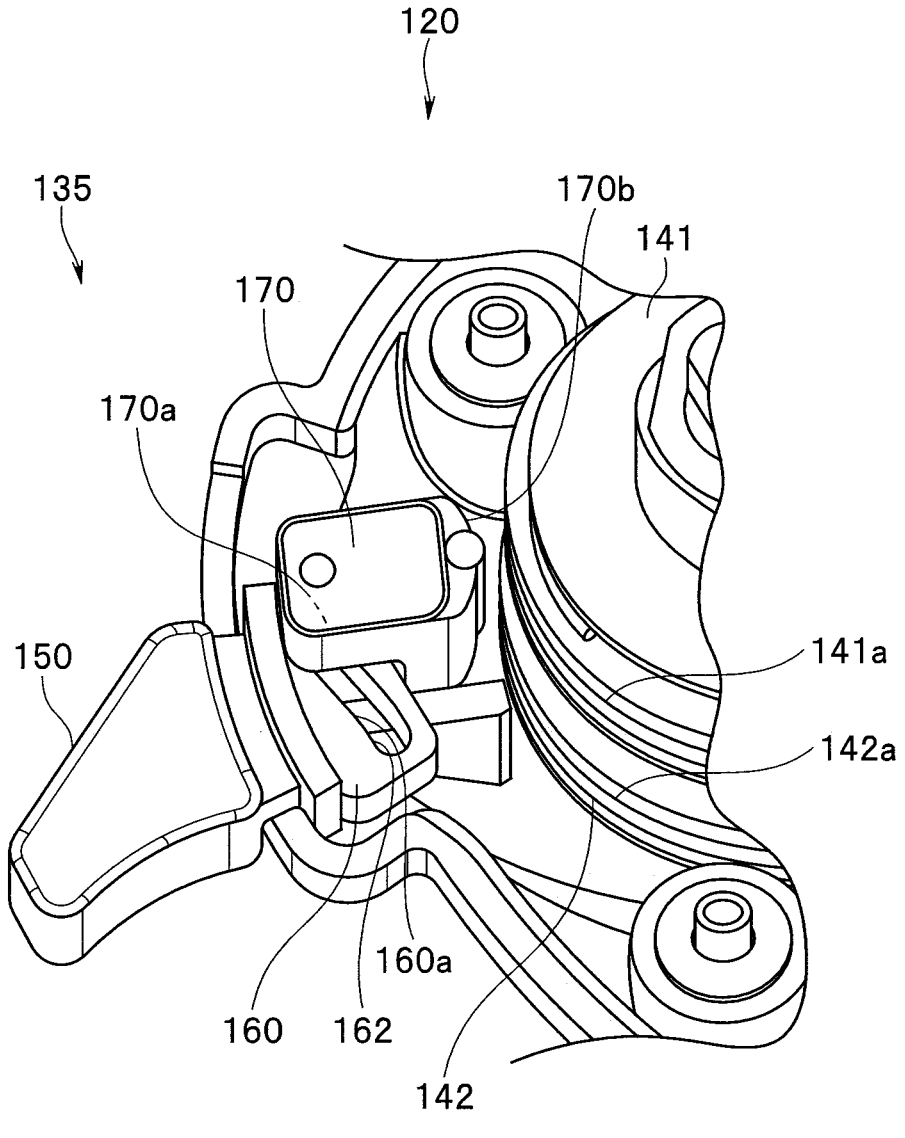
FIG. 12 is a main-part enlarged perspective view of the bending operation mechanism out of the operation portion of a baby endoscope according to a third embodiment of the present invention, illustrating the unlocked state of the bending operation mechanism.
Figure 13:
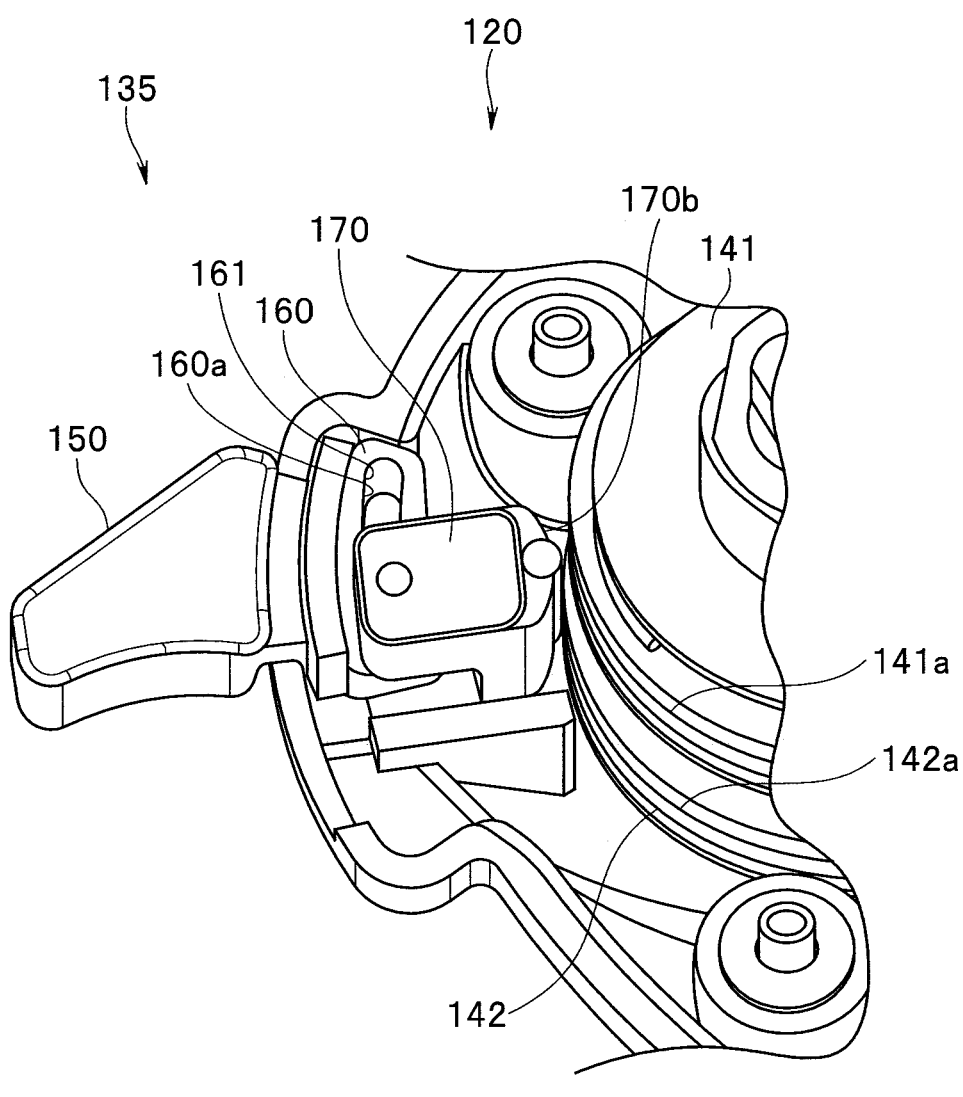
FIG. 13 is a main-part enlarged perspective view of the bending operation mechanism out of the operation portion of the baby endoscope according to the third embodiment, illustrating the locked state of the bending operation mechanism.

FIGS. 12 and 13 are diagrams illustrating the bending operation mechanism out of the operation portion of the baby endoscope according to the third embodiment of the present invention. FIG. 12 is a main-part enlarged perspective view illustrating the unlocked state of the bending operation mechanism. FIG. 13 is a main-part enlarged perspective view illustrating the locked state of the bending operation mechanism.

Similarly to the first embodiment, the bending operation mechanism 135 in the third embodiment includes the UD bending operation handle 31 for an operation to bend the bending portion 24 in the first axial direction (U/D direction), and the RL bending operation handle 32 for an operation to bend the bending portion 24 in the second axial direction (R/L direction) orthogonal to the first axial direction. The bending operation mechanism 135 also includes a first pulley 141 that acts in cooperation with the UD bending operation handle 31, and a second pulley 142 that acts in cooperation with the RL bending operation handle 32. The bending operation mechanism 135 additionally includes a lock lever 150 for controlling rotation of the first pulley 141 and the second pulley 142.

The bending operation mechanism 135 also includes a brake member 170 for restricting rotation of the first pulley 141 and the second pulley 142, and a cam member 160 that engages with the brake member 170 and shifts the brake member 170 in the radial direction of the rotational axis.

The first pulley 141 connected to the first angle wire for an operation to bend the bending portion 24 in the first axial direction (U/D direction), and the second pulley 142 connected to the second angle wire for an operation to bend the bending portion 24 in the second axial direction (R/L direction) orthogonal to the first axial direction are disposed inside the operation portion of the baby endoscope 120 according to the third embodiment.

The first pulley 141 is a wire pulling member for the first angle wire and is coupled to the UD bending operation handle 31 and supported to rotate about the rotational axis of the UD bending operation handle 31 along with rotation of the UD bending operation handle 31.

The first pulley 141 includes an outer peripheral surface 141a having a predetermined radius, and the above-described first angle wire is connected to the outer peripheral surface 141a. In accordance with a rotational operation of the UD bending operation handle 31, the first pulley 141 rotates, the first angle wire is pulled, and the bending portion 24 bends in the first axial direction (U/D direction).

The second pulley 142 is a wire pulling member for the second angle wire and is coupled to the RL bending operation handle 32 and supported to rotate about the rotational axis of the RL bending operation handle 32 along with rotation of the RL bending operation handle 32.

The second pulley 142 includes an outer peripheral surface 142a having a radius substantially equal to the radius of the first pulley 141, and the above-described second angle wire is connected to the outer peripheral surface 142a. In accordance with a rotational operation of the RL bending operation handle 32, the second pulley 142 rotates, the second angle wire is pulled, and the bending portion 24 bends in the second axial direction (R/L direction).

The lock lever 150 is supported to be coaxially rotatable with the UD bending operation handle 31 and the RL bending operation handle 32 described above on the proximal end side of the operation portion. Specifically, the lock lever 150 is supported to be rotatable, independently from the UD bending operation handle 31 and the RL bending operation handle 32, on the first arc having a predetermined radius and having an axis center at the rotational axis 30a.

The lock lever 150 is provided for controlling rotation of the first pulley 141 that acts in cooperation with the UD bending operation handle 31 and the second pulley 142 that acts in cooperation with the RL bending operation handle 32, and configured to shift to an unlocked state position (position illustrated in FIG. 12) at which rotation of the first pulley 141 and the second pulley 142 is not restricted and a locked state position (position illustrated in FIG. 13) at which rotation of the first pulley 141 and the second pulley 142 is restricted.

The cam member 160 is disposed to be rotatable integrally with the above-described rotation of the lock lever 150 and movable, inside the case of the operation portion, on the second arc having an axis center at the rotational axis 30a (and having a radius smaller than the radius of the first arc). The cam member 160 is also disposed outside the first pulley 141 and the second pulley 142 in the radial direction of the rotational axis 30a and includes a cam surface 160a facing the center of the rotational axis 30a.

The cam surface 160a in the third embodiment includes a first cam portion 161 (refer to FIG. 13) including a position separated from the rotational axis 30a by a first distance, and a second cam portion 162 (refer to FIG. 12) including a position separated from the rotational axis 30a by a second distance shorter than the first distance.

The brake member 170 is disposed between the cam surface 160a of the cam member 160 and each of the outer peripheral surface 141a of the first pulley 141 and the outer peripheral surface 142a of the second pulley 142. The brake member 170 includes a cam follower surface 170a capable of sliding relative to the cam surface 160a and includes a contact surface 170b capable of contacting the outer peripheral surface 141a of the first pulley 141 and the outer peripheral surface 142a of the second pulley 142.

When the lock lever 150 rotates from the unlocked state illustrated in FIG. 12 to the locked state illustrated in FIG. 13, the cam follower surface 170a of the brake member 170 slides from the first cam portion 161 toward the second cam portion 162 in the cam surface 160a and the contact surface 170b contacts the outer peripheral surface 141a of the first pulley 141 and the outer peripheral surface 142a of the second pulley 142 and restricts rotation of the first pulley 141 and the second pulley 142.

The contact surface 170b of the brake member 170 in the present embodiment is formed to generate predetermined frictional force at a level sufficient to restrict rotation of the first pulley 141 and the second pulley 142 when contacting the outer peripheral surface 141a of the first pulley 141 and the outer peripheral surface 142a of the second pulley 142.

As described above, similarly to the first embodiment, in the endoscope incorporating the insertion-instrument bending operation mechanism according to the third embodiment, a pulley to which an angle wire for bending the bending portion is connected is pressed in the radial direction of the rotational axis by the brake member, which is disposed on the circumference of the pulley, to restrict rotation of the pulley. Thus, it is possible to reduce the thickness of the operation portion as compared to a configuration including a mechanism configured to press the pulley in the thrust direction, and it is possible to ensure favorable operability without size increase of the operation portion.

<Fixation Band and Fixation Band Hook>

Subsequently, the fixation band 80 for fixing the baby endoscope 20 according to the first embodiment described above to the mother endoscope 10, the fixation band hook 33 of the operation portion 22 with which the fixation band 80 is engaged, and a method of mounting the baby endoscope 20 on the mother endoscope 10 will be described below with reference to FIGS. 14 to 17 in addition to FIGS. 2 and 3.

FIG. 14 is a perspective view illustrating the appearance of the baby endoscope according to the first embodiment together with a fixation band for fixation to the mother endoscope. FIG. 15 is a side view of part of the baby endoscope according to the first embodiment and the operation portion of the mother endoscope, illustrating a state in which the baby endoscope is mounted on the mother endoscope. FIG. 16 is a perspective view illustrating a fixation band used when the baby endoscope according to any of the first to third embodiments is mounted on the mother endoscope. FIG. 17 is a side view illustrating the fixation band used when the baby endoscope according to the first embodiment is mounted on the mother endoscope.

As described above, the fixation band hook 33 for locking the fixation band 80 for mounting the baby endoscope 20 on the mother endoscope 10 is provided beside the bending operation handle portion 30 and the lock lever 50 on the proximal end side of the operation portion 22 of the baby endoscope 20 (refer to FIGS. 2 and 3).

As illustrated in FIGS. 2, 3, and 14, at the operation portion 22 of the baby endoscope 20, the fixation band hook 33 is disposed as a protrusion on the proximal end side (upper side in the drawing) of the rotational axis 30*a* of the UD bending operation handle 31 and the RL bending operation handle 32, on a side opposite to an opening 26*a* of the treatment instrument insertion channel 26 with respect to the rotational axis 30*a*, and on the back surface side of a frame body of the operation portion 22.

As illustrated in FIGS. 16 and 17, the fixation band 80 includes a proximal end portion 80*e* fixed near the pipe sleeve 26*b* for treatment instrument insertion at the operation portion 22, a grasping portion 80*a* provided closer to a distal end portion 80*c* and grasped by the operator, and a hole 80*b* formed on the proximal end side of the grasping portion 80*a*. As illustrated in FIG. 17, the grasping portion 80*a* includes a grasping surface 80*d* having a gradual curved surface shape toward the distal end portion 80*c*, thereby improving grasping easiness.

As illustrated in FIG. 15, the operation portion 22 of the baby endoscope 20 is mounted on the lower part of the operation portion 12 of the mother endoscope 10 by using the fixation band 80 as described above. When mounting the baby endoscope 20 on the mother endoscope 10, the operator first fixes the proximal end portion 80*e* of the fixation band 80 on the pipe sleeve 26*b* side for treatment instrument insertion at the operation portion 22, and then winds the fixation band 80, the proximal end portion of which is fixed, around the operation portion 12 of the mother endoscope 10.

In addition, the operator grasps the grasping portion 80*a* of the fixation band 80 wound around the operation portion 12 of the mother endoscope 10 and engages the hole 80*b* formed on the proximal end side of the grasping portion 80*a* with the fixation band hook 33 provided at the operation portion 22. Accordingly, the operation portion 22 of the baby endoscope 20 is fixed to the operation portion 12 of the mother endoscope 10.

Note that the grasping portion 80*a* of the fixation band 80 includes the grasping surface 80*d* having a gradual curved surface shape toward the distal end portion 80*c* and has a relatively large area, which improves operability of mounting the baby endoscope 20 on the mother endoscope 10.

In the present embodiment, when the fixation band 80 is engaged with the fixation band hook 33 through the hole 80*b*, the grasping portion 80*a* is disposed at a position where the grasping portion 80*a* does not interfere with operations of the UD bending operation handle 31, the RL bending operation handle 32, and the lock lever 50.

<Housing Container of Baby Endoscope>

Subsequently, a container in which the baby endoscope 20 according to the first embodiment described above is housed will be described below.

Figure 18:
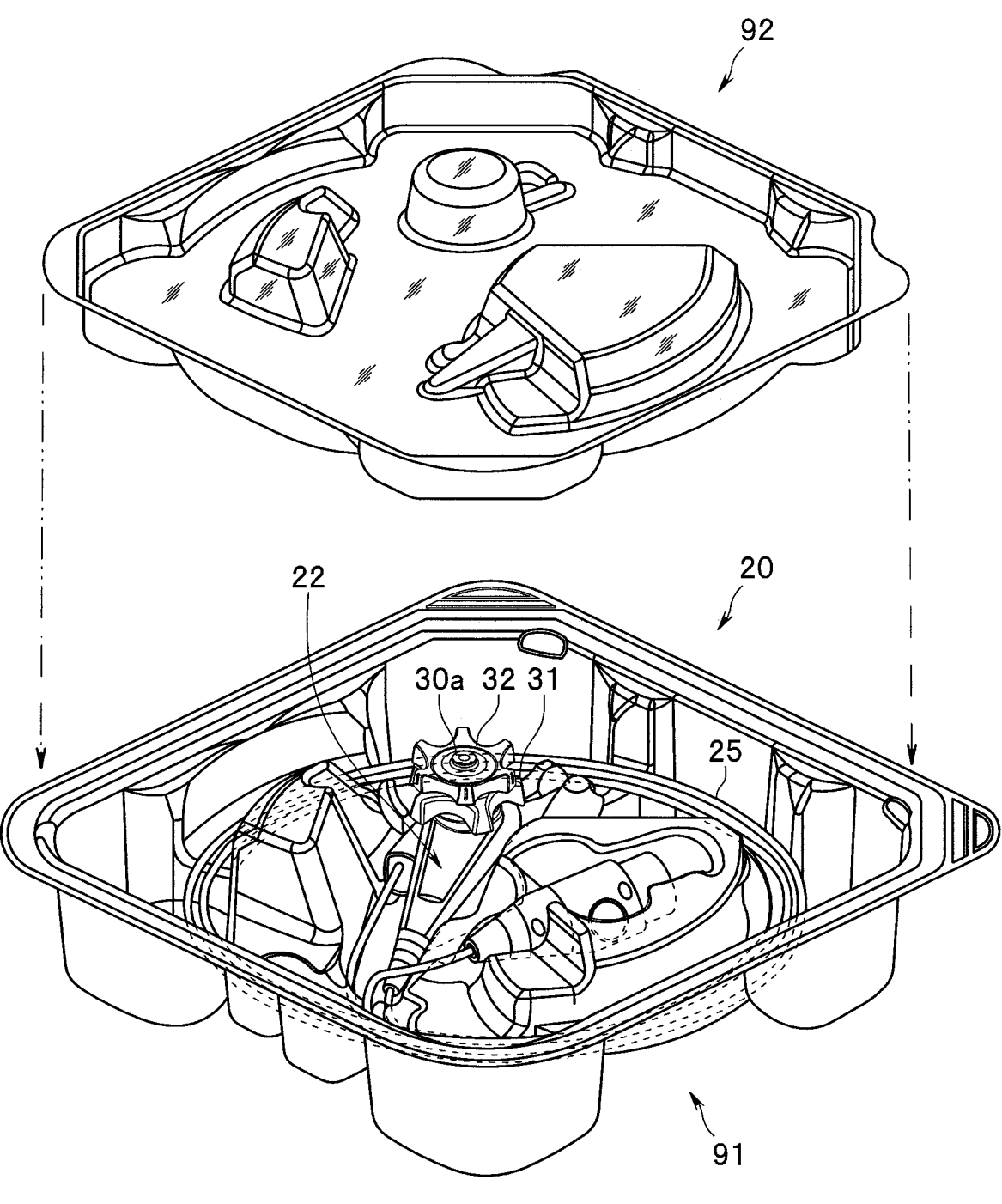
FIG. 18 is a perspective view illustrating a container in which the baby endoscope according to the first embodiment is housed.

FIG. 18 is a perspective view illustrating the container in which the baby endoscope according to the first embodiment is housed.

As illustrated in FIG. 18, the above-described container in which the baby endoscope 20 is housed includes a base portion 91 formed of transparent resin and a lid unit 92 that engages with the base portion 91. The base portion 91 is provided with cutouts for housing components of the baby endoscope 20, in other words, the operation portion 22, the insertion portion 21 (including the flexible tube portion 25), the universal cable 27, and the endoscope connector 28.

When the baby endoscope 20 is housed in the base portion 91, the UD bending operation handle 31 and the RL bending operation handle 32 of the operation portion 22 are positioned facing upward and the flexible tube portion 25 of the insertion portion 21 is placed in an anticlockwise loop.

When the baby endoscope 20 is taken out of the base portion 91 and mounted on the mother endoscope 10 as illustrated in FIG. 3 after the baby endoscope 20 is disposed in the base portion 91 as described above, in other words, the flexible tube portion 25 of the insertion portion 21 is placed in an anticlockwise loop in a state in which the operation portion 22 is positioned facing upward, the flexible tube portion 25 can form a loop in a direction naturally separating from the operator, which can provide excellent operability.

The present invention is not limited to the above-described embodiments but may be, for example, changed or modified in various manners without departing from the gist of the invention.

What is claimed is:

1. An operation body for use with an insertion-instrument, the operation body comprising:
   a pulley having a first outer circumferential surface, the pulley configured to rotate about a rotational axis to bend a bending portion;
   a lock operation member configured to rotate about the rotational axis, the lock operation member comprising a cam having a cam surface positioned radially outside the first outer circumferential surface; and
   a brake member having an inner circumferential brake surface disposed between the first outer circumferential surface and the cam surface;
   wherein when the cam surface is rotated, the inner circumferential brake surface is configured to move into direct contact with the first outer circumferential surface of the pulley along a circumferential length of the inner circumferential brake surface to restrict rotation of the pulley.

2. The operation body according to claim 1, wherein
   the cam is configured to rotate along the first outer circumferential surface of the pulley, and
   the brake member moves in a radial direction of the pulley in response to rotation of the cam.

3. The operation body according to claim 2, wherein
   the brake member includes a first portion having a first thickness and a second portion having a second thickness, the second thickness is larger than the first thickness, and
   the brake member is configured to restrict a rotation of the pulley when the cam rotates from being adjacent to the first portion of the brake member to the cam being adjacent to the second portion of the brake member.

4. The operation body according to claim 2, wherein
the pulley has first irregularities, and
the brake member has second irregularities configured to
mesh with the first irregularities when the brake mem-
ber moves in the radial direction in response to rotation
of the cam.

5. The operation body according to claim 1, wherein the
pulley is a first pulley, the first outer circumferential surface
is a first outer circumferential surface of the first pulley,
the operation body further comprising:
a first handle configured to rotate about the rotational
axis and configured to bend the bending portion in a
first direction, the bending portion being provided at
an insertion portion; and
a second handle rotatably supported about the rota-
tional axis and configured to bend the bending por-
tion in a second direction; and
a second pulley configured to rotate about the rotational
axis to bend the bending section, the second pulley
having a first outer circumferential surface of the
second pulley,
wherein the brake member is disposed between the first
outer circumferential surface of the second pulley and
the cam surface to restrict rotation of the first pulley and
restrict rotation of the second pulley when the cam
surface is rotated.

6. The operation body according to claim 1, wherein the
first outer circumferential surface having a constant outer
diameter.

7. An operation body comprising:
a pulley having a first outer circumferential surface, the
pulley configured to rotate about a rotational axis to
bend a bending portion;
a cam configured to rotate about the rotational axis, the
cam having a cam surface positioned radially outside
the first outer circumferential surface; and
an inner circumferential brake surface movably disposed
between the first outer circumferential surface of the
pulley and the cam surface;
wherein when the cam surface is rotated, the inner cir-
cumferential brake surface is configured to move into
direct contact with the first outer circumferential sur-
face of the pulley along a circumferential length of the
inner circumferential brake surface to restrict rotation
of the pulley.

8. The operation body according to claim 7, wherein
the cam is configured to rotate along the first outer
circumferential surface of the pulley, and
the inner circumferential brake surface moves in a radial
direction of the pulley in response to rotation of the
cam.

9. The operation body according to claim 8, further
comprising a brake having the inner circumferential brake
surface;
wherein the brake includes a first portion having a first
thickness and a second portion having a second thick-
ness, the second thickness is larger than the first thick-
ness, and
the inner circumferential brake surface is configured to
restrict rotation of the pulley when the cam rotates from
being adjacent to the first portion of the inner circum-
ferential brake surface to the cam being adjacent to the
second portion of the inner circumferential brake sur-
face.

10. The operation body according to claim 8, wherein the
inner circumferential brake surface has first irregularities
configured to restrict rotation of the pulley when the brake
moves in the radial direction in response to rotation of the
cam.

11. The operation body according to claim 10, wherein the
pulley has second irregularities configured to mesh with the
first irregularities of the inner circumferential brake surface
when the brake member moves in the radial direction in
response to rotation of the cam.

12. The operation body according to claim 7, wherein the
pulley is a first pulley, the first outer circumferential surface
is a first outer circumferential surface of the first pulley,
the operation body further comprising:
a first bending operation handle configured to rotate
about the rotational axis and configured to bend the
bending portion in a first direction, the bending
portion being provided at an insertion portion; and
a second bending operation handle configured to rotate
about the rotational axis and configured to bend the
bending portion in a second direction; and
a second pulley configured to rotate about the rotational
axis to bend the bending section, the second pulley
having a first outer circumferential surface of the
second pulley,
wherein the inner circumferential brake surface is dis-
posed between the first outer circumferential surface of
the second pulley and the cam surface to restrict
rotation of the first pulley and restrict rotation of the
second pulley when the cam surface is rotated.

13. The operation body according to claim 7, wherein
the pulley is configured to be switched between an
unlocked configuration and a locked configuration,
in the unlocked configuration, the inner circumferential
brake surface is spaced apart from the first outer
circumferential surface of the pulley to allow rotation
of the pulley, and
in the locked configuration, the inner circumferential
brake surface contacts with the first outer circumfer-
ential surface of the pulley to restrict rotation of the
pulley.

14. The operation body according to claim 13, wherein
in the unlocked configuration, the cam is positioned at a
first radial position relative to the rotational axis and a
first circumferential position relative to the first outer
circumferential surface, and
in the locked configuration, the cam is positioned at a
second radial position relative to the rotational axis and
a second circumferential position relative to the first
outer circumferential surface.

15. The operation body according to claim 14, wherein a
first distance from the first radial position to the rotational
axis is the same as a second distance from the second radial
position to the rotational axis.

16. The operation body according to claim 7, wherein the
first outer circumferential surface having a constant outer
diameter.

17. An insertion instrument comprising:
an insertion portion; and
the operation body according to claim 7, the operation
body provided proximally relative to the insertion
portion.

18. The insertion instrument according to claim 17, fur-
ther comprising a lock lever configured to rotate about the
rotational axis to rotate the cam.

19. The insertion instrument according to claim 18, wherein the pulley includes a second circumferential surface configured to contact an angle bending wire, the second circumferential surface being adjacent to the first outer circumferential surface, the lock lever includes the cam, the lock lever configured to rotate about the rotational axis, and the inner circumferential brake surface configured to contact with the first outer circumferential surface of the pulley in response to rotation of the lock lever.

20. The insertion instrument according to claim 18, wherein the lock lever is provided at an opposite side of the insertion portion with respect to the pulley.

\* \* \* \* \*